US006855925B2

(12) United States Patent
Ellson et al.

(10) Patent No.: US 6,855,925 B2
(45) Date of Patent: *Feb. 15, 2005

(54) METHODS, DEVICES, AND SYSTEMS USING ACOUSTIC EJECTION FOR DEPOSITING FLUID DROPLETS ON A SAMPLE SURFACE FOR ANALYSIS

(75) Inventors: Richard N. Ellson, Palo Alto, CA (US); Mitchell W. Mutz, Palo Alto, CA (US); Richard Michael Caprioli, Brentwood, TN (US)

(73) Assignee: Picoliter Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/379,379

(22) Filed: Mar. 3, 2003

(65) Prior Publication Data

US 2004/0026615 A1 Feb. 12, 2004

Related U.S. Application Data

(63) Continuation-in-part of application No. 10/157,755, filed on May 28, 2002, now Pat. No. 6,707,038, which is a continuation-in-part of application No. 10/087,372, filed on Mar. 1, 2002, which is a continuation-in-part of application No. 10/066,546, filed on Jan. 30, 2002, now Pat. No. 6,710,335, which is a continuation-in-part of application No. 09/784,705, filed on Feb. 14, 2001, now Pat. No. 6,603,118.

(51) Int. Cl.[7] .......................... H01J 49/04; G01N 1/10; G01N 35/10
(52) U.S. Cl. ...................... 250/288; 436/180; 422/100; 422/63; 435/30; 73/864; 73/864.81
(58) Field of Search ........................... 250/288; 422/63, 422/100; 435/30, 325, 40; 436/180; 73/864

(56) References Cited

U.S. PATENT DOCUMENTS 4,308,547 A  12/1981  Lovelady et al.
4,751,529 A  6/1988  Elrod et al.

(List continued on next page.)

FOREIGN PATENT DOCUMENTS

EP  0434931 A2  7/1991

OTHER PUBLICATIONS

U.S. Appl. No. 09/669,267, filed Sep. 25, 2000, Ellson.
U.S. Appl. No. 09/669,996, filed Sep. 25, 2000, Ellson et al.

(List continued on next page.)

Primary Examiner—Jack I. Berman
(74) Attorney, Agent, or Firm—Dianne E. Reed; Reed Intellectual Property Law Group

(57) ABSTRACT

Provided is a method for preparing a sample surface for analysis that involves placing a sample surface in droplet-receiving relationship to a reservoir containing an analysis-enhancing fluid. Typically, the analysis-enhancing fluid is comprised of a mass spectrometry matrix material and a carrier fluid, and the carrier fluid is comprised of a low volatility solvent. A droplet of the analysis-enhancing fluid from the reservoir such that the droplet is deposited on the sample surface at a designated site. Such ejection is typically, but not necessarily carried out through the application of focused acoustic energy. Then, the sample is subjected to conditions sufficient to allow the analysis-enhancing fluid to interact with the sample surface to render the sample surface suitable for analysis. Optionally, the sample is analyzed at the selected site. Also provided are systems and devices for preparing a sample surface for analysis.

69 Claims, 5 Drawing Sheets

U.S. PATENT DOCUMENTS

| | | | |
|---|---|---|---|
| 5,041,849 | A | 8/1991 | Quate et al. |
| 5,306,412 | A | 4/1994 | Whitehouse et al. |
| 5,520,715 | A | 5/1996 | Oeftering |
| 5,722,479 | A | 3/1998 | Oeftering |
| 5,798,779 | A | 8/1998 | Nakayasu et al. |
| 5,808,300 | A | 9/1998 | Caprioli |
| 5,808,636 | A | 9/1998 | Stearns |
| 5,877,580 | A | 3/1999 | Swierkowski |
| 6,245,297 | B1 * | 6/2001 | Kowallis .................... 422/100 |
| 6,291,820 | B1 | 9/2001 | Hamza et al. |
| 6,322,970 | B1 | 11/2001 | Little et al. |
| 6,327,030 | B1 | 12/2001 | Ifju et al. |
| 6,465,778 | B1 * | 10/2002 | Koster et al. ............... 250/288 |
| 6,603,118 | B2 * | 8/2003 | Ellson et al. ............... 250/288 |
| 2002/0037579 | A1 | 3/2002 | Ellson et al. |
| 2002/0061258 | A1 | 5/2002 | Mutz et al. |
| 2002/0064808 | A1 | 5/2002 | Mutz et al. |
| 2002/0064809 | A1 | 5/2002 | Mutz et al. |
| 2002/0090720 | A1 | 7/2002 | Mutz et al. |
| 2002/0094582 | A1 | 7/2002 | Williams et al. |
| 2002/0125424 | A1 | 9/2002 | Ellson et al. |
| 2002/0171037 | A1 | 11/2002 | Ellson et al. |
| 2002/0195558 | A1 | 12/2002 | Ellson et al. |
| 2003/0148538 | A1 * | 8/2003 | Ng ............................. 436/180 |

OTHER PUBLICATIONS

U.S. Appl. No. 09/669,997, filed Sep. 25, 2000, Mutz et al.

U.S. Appl. No. 09/999,166, filed Nov. 29, 2001, Mutz et al.

Amemiya et al. (1997), *Proceedings of the 1997 IS&T's NIP 13: 1997 International Conference on Digital Printing Technologies*, pp. 698–702.

IUPAC–IUB Commission on Biochemical Nomenclature (CBN) (1970), "Abbreviations and Symbols for Nucleic Acids, Polynucleotides and Their Constituents," *Biochemistry 9*(20):4022–4025.

Karas et al. (1998), "Laser Desorption Ionization of Proteins with Molecular Masses Exceeding 10,000 Daltons," *Anal. Chem. 60*:2299–2301.

Steel et al. (2000), "The Flow–Thru Chip™: A Three–Dimensional Biochip Platform," *Microarray Biochip Technology*, Chapter 5, pp. 87–117, BioTechniques Books, Natick, MA.

Stoeckli et al.(2001), "Imaging Mass Spectrometry: A New Technology for the Analysis of Protein Expression in Mammalian Tissues," *Nature Medicine 7*(4):493–496.

* cited by examiner

METHODS, DEVICES, AND SYSTEMS USING ACOUSTIC EJECTION FOR DEPOSITING FLUID DROPLETS ON A SAMPLE SURFACE FOR ANALYSIS

CROSS-REFERENCE TO RELATED APPLICATIONS

This is a continuation-in-part of U.S. patent application Ser. No. 10/157,755, filed May 28, 2002 now U.S. Pat. No. 6,707,038, which is a continuation-in-part of U.S. patent application Ser. No. 10/087,372, filed Mar. 1, 2002, which is a continuation-in-part of U.S. patent application Ser. No. 10/066,546, filed Jan. 30, 2002 now U.S. Pat. No. 6,710,335, which is a continuation-in-part of U.S. patent application Ser. No. 09/784,705, filed Feb. 14, 2001 now U.S. Pat. No. 6,603,118, the disclosures of which are incorporated by reference herein.

TECHNICAL FIELD

This invention relates generally to methods, devices, and systems for depositing fluids on a surface of a sample. More particularly, the invention relates to the use of nozzleless acoustic ejection to deposit droplets of analysis-enhancing fluid on designated sites of a sample surface. The invention is especially useful in mass spectrometric imaging of tissue surfaces and for facilitating the compositional analysis of biological samples.

BACKGROUND

Mass spectrometry is a well-established analytical technique in which sample molecules are ionized and the resulting ions are sorted by mass-to-charge ratio. Advances in mass spectrometry have made it possible to obtain detailed information regarding a wide variety of sample surface types. In the semiconductor industry, for example, secondary ion mass spectrometry is used to determine the composition of microscopic regions of wafer surfaces. As another example, in the biotechnology arena, surface-based mass spectrometry is used to analyze single nucleotide polymorphisms in microarray formats. See, e.g., U.S. Pat. No. 6,322,970 to Little et al.

Matrix-Assisted Laser Desorption Ionization (MALDI) is an ionization technique commonly used for mass spectrometric analysis of large and/or labile biomolecules, such as nucleotidic and peptidic oligomers, polymers, and dendrimers, as well as for analysis of non-biomolecular compounds, such as fullerenes. MALDI is considered a "soft" ionizing technique in which both positive and negative ions are produced. The technique involves depositing a small volume of sample fluid containing an analyte on a substrate comprised of a photon-absorbing matrix material selected to enhanced desorption performance. See Karas et al. (1988), "Laser Desorption Ionization of Proteins with Molecular Masses Exceeding 10,000 Daltons," *Anal. Chem.* 60:2299–2301. The matrix material is usually a crystalline organic acid that absorbs electromagnetic radiation near the wavelength of the laser. When co-crystallized with analyte, the matrix material assists in the ionization and desorption of analyte moieties. The sample fluid typically contains a solvent and the analyte. Once the solvent has been evaporated from the substrate, the analyte remains on the substrate at the location where the sample fluid is deposited. Photons from a laser strike the substrate at the location of the analyte and, as a result, ions and neutral molecules are desorbed from the substrate. MALDI techniques are particularly useful in providing a means for efficiently analyzing a large number of samples. In addition, MALDI is especially useful in the analysis of minute amounts of sample that are provided over a small area of a substrate surface.

Surface Enhanced Laser Desorption Ionization (SELDI) is another example of a surface-based ionization technique that allows for high-throughput mass spectrometry. SELDI uses affinity-capture reagents, such as antibodies, to collect samples from a complex mixture, which allows in situ purification of the analyte followed by conventional MALDI analysis. Typically, SELDI is used to analyze complex mixtures of proteins and other biomolecules. SELDI employs a chemically reactive surface such as a "protein chip" to interact with analytes, e.g., proteins, in solution. Such a surface selectively interacts with analytes and immobilizes them thereon. Thus, analytes can be partially purified on the chip and then quickly analyzed in the mass spectrometer. By providing different reactive moieties at different sites on a substrate surface, throughput may be increased.

Recently, mass spectrometry techniques involving laser desorption have been adapted for cellular analysis. Cellular assays such as mass spectrometry are carried out to provide critical information for the understanding of complex cell functions. U.S. Pat. No. 5,808,300 to Caprioli, for example, describes a method for imaging biological samples with mass spectrometry using surface-based ionization. This method allows users to measure the distribution of a specific element or small molecule within biological specimens such as tissue slices or individual cells. In particular, the method can be used for the analysis of specific peptides in whole cells, e.g., by obtaining signals for peptides and proteins directly from tissues and blots of tissues. In addition, the method has been used to desorb relatively large proteins from tissues and blots of tissues in the molecular weight range beyond about 80 kilodaltons. From such samples, hundreds of peptide and protein peaks can be recorded in the mass spectrum produced from a single laser-ablated site on the sample. When a laser ablates the surface of a sample at multiple sites and the mass spectrum from each site is saved separately, a data array is produced, which contains the relative intensity of any given mass at each site. An image of the sample surface can then be constructed for any given molecular weight, effectively representing a compositional map of the sample surface.

One important issue to successful MALDI and MALDI-like profiling and imaging as described above is the controlled application of a mass-spectrometry matrix material to the tissue surface, either as a series of features or as a continuous coating so as to provide mass spectrometry matrix material at each site of laser ablation. For example, as described in U.S. Pat. No. 5,808,300 to Caprioli, the mass spectrometry matrix material may be applied as a continuous and uniform coating of less than about 50 micrometers in thickness. In order to apply the mass spectrometry matrix material in a controlled manner, carefully metered amounts of sample fluids should be accurately and precisely placed on a sample surface. The ability to closely compare relative abundances of a given protein between two tissues is dependent on the application of matrix in exactly the same way to both tissues.

Most current small-volume dispensing techniques, however, are not suitable for precise and reproducible matrix material application, due to limitations in volume or in accuracy of placement. For example, capillaries having a small interior channel (e.g., Eppendorf-type capillaries) are often used to transfer fluids from a pool of fluid. Their tips are submerged in the pool in order to draw fluid therefrom.

In order to provide sufficient mechanical strength for handling, however, such capillaries must have a large wall thickness as compared to the interior channel diameter. Thus, the physical dimensions of such capillaries limit their fluid-handling capability. In addition, since any wetting of the exterior capillary surface results in fluid waste, the high ratio of wall thickness to channel diameter exacerbates fluid waste. Also, the pool has a minimum required volume determined not by the fluid introduced into the capillary but, rather, by the need to immerse the large exterior dimension of the capillary. As a result, the fluid volume required for capillary submersion may be more than an order of magnitude larger than the fluid volume transferred into the capillary.

A number of patents have described the use of acoustic energy in printing. For example, U.S. Pat. No. 4,308,547 to Lovelady et al. describes a liquid drop emitter that utilizes acoustic principles in ejecting droplets from a body of liquid ink onto a moving document to form characters or bar codes thereon. As described in a number of U.S. patent applications, acoustic ejection provides for highly accurate deposition of minute volumes of fluids on a surface, wherein droplet volume—and thus "spot" size on the substrate surface—can be carefully controlled, and droplets can be precisely directed to particular sites on a substrate surface. See, e.g., U.S. Patent Application Publication No. 2002037579 to Ellson et al. In other words, nozzleless fluid delivery provides high fluid-delivery efficiency through accurate and precise droplet placement. Nozzleless fluid ejection also provides a high level of control over ejected droplet size.

Acoustic ejection is a technique that is well suited for depositing minute volumes of fluids on a surface because the technique allows for control over droplet volume and thus "spot" size on the surface, as well as control over the trajectory of ejected droplets and the precise location of the deposition sites on the surface. See, e.g., U.S. Patent Application Publication No. 20020037579 to Ellson et al. While nozzleless fluid ejection has generally been appreciated for ink printing applications, acoustic deposition is a generally unknown technique in the field of cellular analysis. Recently, focused acoustic energy has been used to manipulate cells and engage in cell sorting. See U.S. Patent Application Publication Nos. 20020064808, 20020064809, 20020090720, and 20020094582 to Mutz et al. In addition, as cellular assays often involve the immobilization of sample cells on a substrate surface and the controlled exposure of the cells to one or more fluids, there exist opportunities to improve cellular assay and analysis techniques through the use of acoustic ejection, particularly when such assays require the precise and accurate handling of small volumes of fluid. For example, U.S. Patent Application Publication No. 20020171037 to Ellson et al. describes the use of acoustic ejection for preparing and analyzing a cellular sample surface. Nozzleless acoustic ejection is used to deposit mass spectrometry matrix material at designated sites on a sample surface to form either a uniform matrix material layer or an array of individual sites. In addition, U.S. Patent Application Publication No. 20020195538 to Ellson et al. describes the use of acoustic ejection to selectively deposit analysis-enhancing fluid according to the surface characteristics of the cellular samples.

As alluded to above, conventional analysis-enhancing fluids for use in mass spectrometry are typically comprised of a mass spectrometry matrix material dissolved in a volatile carrier fluid. Once deposited on a sample surface, the carrier fluid is evaporated, thereby allowing the matrix material to precipitate and crystallize with the sample. It has recently been discovered, however, that such conventional analysis-enhancing fluids are not optimal for use in mass spectrometry when dispensed as low-volume droplets under ordinary dispensing conditions, because such fluids do not allow the matrix material to properly crystallize with the sample.

Accordingly, there is a need for methods and systems that overcome the disadvantages and limitations associated with previously known technologies.

SUMMARY OF THE INVENTION

Accordingly, one embodiment of the invention relates to method for preparing a sample surface for analysis. In general, a reservoir containing an analysis-enhancing fluid is provided, and a surface of a sample is placed in droplet-receiving relationship to the fluid-containing reservoir. In some instances, the reservoir has a volume no greater than 100 nL, and the sample is a cellular sample. A droplet of the analysis-enhancing fluid from the reservoir such that the droplet is deposited on the sample surface at a designated site. Such ejection is typically, but not necessarily carried out through the application of focused acoustic energy. Then, the sample is subjected to conditions sufficient to allow the analysis-enhancing fluid to interact with the sample surface to render the sample surface suitable for analysis. Optionally, the sample is analyzed at the selected site.

Typically, the analysis-enhancing fluid is comprised of an analysis-enhancing moiety and a carrier fluid. In some instances, the carrier fluid is comprised of a low volatility solvent that has a boiling point greater than 100° C. at a pressure of 1 atmosphere. In addition, the carrier fluid may further comprise a high volatility solvent that has a boiling point less than 100° C. at a pressure of 1 atmosphere. The analysis-enhancing moiety may comprise a mass spectrometry matrix material. In such a case, energy is applied to the designated site in a manner effective to release sample molecules from the sample surface for analysis, e.g., MALDI-TOF mass spectrometric analysis.

The invention is particularly suited for instances in which the ejected droplet has a small volume to as to control the rate of solvent evaporation. Typically, the volume of the ejected droplet is no greater than about 50 pL. Preferably, the volume of the ejected droplet is no greater than about 10 pL More preferably, the volume of the ejected droplet is no greater than about 1 pL. Optimally, the volume of the ejected droplet is less than about 1 pL, e.g., in the range of about 0.025 pL to about 1 pL.

There are a number of ways to subject the sample to conditions sufficient to allow the analysis-enhancing fluid to interact with the sample surface to render the sample surface suitable for analysis. When the analysis-enhancing fluid is comprised of a low volatility solvent, the sample may be subjected to a temperature greater than 25° C. and/or to a pressure lower than about 1 atmosphere. When the analysis-enhancing fluid is comprised of a high volatility solvent, the sample may be subjected to a temperature lower than 25° C. and/or a pressure greater than 1 atmosphere. In some instances, the sample to an atmosphere that is at least about 30% saturated with the carrier fluid. In addition or in the alternative, the sample is subjected to conditions such that the carrier fluid exhibits a volatility quotient of at least about 30.

The invention also provides a system for depositing an analysis-enhancing fluid on a surface of a sample. The system is comprised of a reservoir containing an analysis-enhancing fluid as described above, an acoustic ejector comprising an acoustic radiation generator for generating acoustic radiation and a focusing means for focusing the acoustic radiation generated, a means for positioning the acoustic ejector in acoustic coupling relationship to the reservoir; and a means for positioning the sample such that a designated site on the sample surface is positioned in droplet-receiving relationship to the reservoir. Optionally, the system may further comprise a means, e.g., a laser, for applying energy to the designated site to effect release and ionization of sample molecules from the sample surface for analysis, and an analyzer, e.g., a mass spectrometer, positioned to receive ionized sample molecules released from the sample surface.

BRIEF DESCRIPTION OF THE DRAWINGS

The invention is described in detail below with reference to the following drawings, wherein like reference numerals indicate a corresponding structure throughout the several views. The figures illustrate aspects of the invention that involve the analysis of a tissue sample through laser desorption-based mass spectrometry.

DETAILED DESCRIPTION OF THE INVENTION

Figure 1:
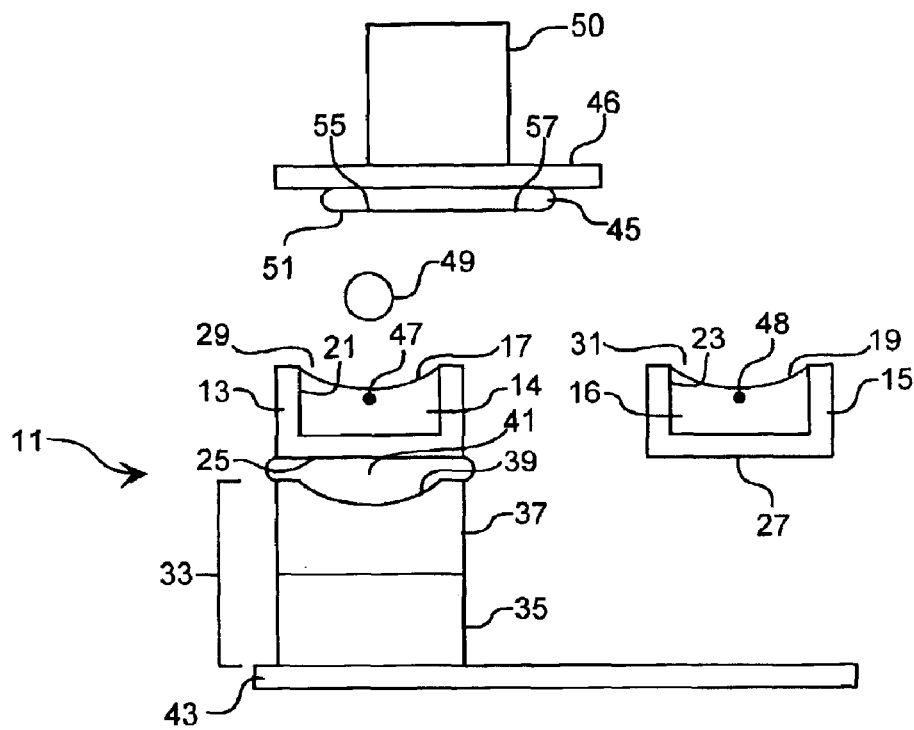
FIG. 1 schematically illustrates the deposition of a first analysis-enhancing fluid on a surface of a tissue sample at a first site.

Definitions and Overview:

Before describing the present invention in detail, it is to be understood that this invention is not limited to specific fluids, biomolecules, or device structures, as such may vary. It is also to be understood that the terminology used herein is for the purpose of describing particular embodiments only, and is not intended to be limiting.

It must be noted that, as used in this specification and the appended claims, the singular forms "a," "an," and "the" include both singular and plural referents unless the context clearly dictates otherwise. Thus, for example, reference to "a reservoir" includes a plurality of reservoirs as well as a single reservoir, reference to "a fluid" includes a mixture of fluids as well as a single fluid, reference to "a biomolecule" includes a combination of biomolecules as well as a single biomolecule, reference to "a characteristic" includes a plurality of characteristics as well as a single characteristic, and the like.

In describing and claiming the present invention, the following terminology will be used in accordance with the definitions set out below.

The terms "acoustic coupling" and "acoustically coupled" as used herein refer to a state wherein an object is placed in direct or indirect contact with another object so as to allow acoustic radiation to be transferred between the objects without substantial loss of acoustic energy. When two items are indirectly acoustically coupled, an "acoustic coupling medium" is needed to provide an intermediary through which acoustic radiation may be transmitted. Thus, an ejector may be acoustically coupled to a fluid, e.g., by immersing the ejector in the fluid or by interposing an acoustic coupling medium between the ejector and the fluid to transfer acoustic radiation generated by the ejector through the acoustic coupling medium and into the fluid.

The terms "acoustic radiation" and "acoustic energy" are used interchangeably herein and refer to the emission and propagation of energy in the form of sound waves. As with other waveforms, acoustic radiation may be focused using a focusing means, as discussed below.

The term "adsorb" as used herein refers to the noncovalent retention of a molecule or a cell by a surface. That is, adsorption occurs as a result of noncovalent interaction between a surface and adsorbing moieties present on the molecule. Adsorption may occur through hydrogen bonding, van der Waal's forces, polar attraction, or electrostatic forces (i.e., through ionic bonding). Examples of adsorbing moieties include, but are not limited to, amine groups, carboxylic acid moieties, hydroxyl groups, nitroso groups, sulfones, and the like.

The term "adsorb" is often used in the context of substrate or sample surfaces. The substrate or sample surface commonly may be functionalized with adsorbent moieties to interact in a certain manner, as when the surface is functionalized with amino groups to render it positively charged in a pH-neutral aqueous environment. Likewise, adsorbate moieties may be added in some cases to effect adsorption, as when a basic protein is fused with an acidic peptide sequence to render adsorbate moieties that can interact electrostatically with a positively charged adsorbent moiety.

The term "array" as used herein refers to a two-dimensional arrangement of features, such as an arrangement of reservoirs (e.g., wells in a well plate) or an arrangement of fluid droplets or molecular moieties on a substrate surface (as in an oligonucleotide or peptide array). Arrays are generally comprised of features regularly ordered in, for example, a rectilinear grid, parallel stripes, spirals, and the like, but non-ordered arrays may be advantageously used as well. An array differs from a pattern in that patterns do not necessarily contain regular and ordered features. In addition, arrays and patterns formed by the deposition of ejected droplets on a surface, as provided herein, are usually substantially invisible to the unaided human eye. Arrays typically, but do not necessarily, comprise at least about 4 to about 10,000,000 features, generally in the range of about 4 to about 1,000,000 features.

The term "attached," as in, for example, a substrate surface having a molecular moiety "attached" thereto, includes covalent binding, adsorption, and physical immobilization. The terms "binding" and "bound" as used herein are identical in meaning to the term "attached."

The terms "biomolecule" and "biological molecule" are used interchangeably herein to refer to any organic molecule—whether naturally occurring, recombinantly produced, or chemically synthesized in whole or in part—that is, was, or can be a part of a living organism. The terms encompass, for example, nucleotides, amino acids, and monosaccharides, as well as oligomeric and polymeric species such as oligonucleotides and polynucleotides; peptidic molecules such as oligopeptides, polypeptides, and proteins; polysaccharides such as disaccharides, oligosaccharides, mucopolysaccharides, and peptidoglycans (peptidopolysaccharides); and the like. The terms also encompass ribosomes, enzyme cofactors, pharmacologically active agents, and the like.

It will be appreciated that, as used herein, the terms "nucleoside" and "nucleotide" refer to nucleosides and nucleotides containing not only the conventional purine and pyrimidine bases, i.e., adenine (A), thymine (T), cytosine (C), guanine (G), and uracil (U), but also protected forms thereof, e.g., wherein the base is protected with a protecting group such as acetyl, difluoroacetyl, trifluoroacetyl, isobutyryl, or benzoyl, and purine and pyrimidine analogs. Suitable analogs will be known to those skilled in the art and are described in the pertinent texts and literature. The terms "peptide," "peptidyl," and "peptidic" as used throughout the specification and claims are intended to include any structure comprised of two or more amino acids. For the most part, the peptides in the present arrays comprise about 5 to 10,000 amino acids, preferably about 5 to 1,000 amino acids. The amino acids forming all or a part of a peptide may be any of the twenty conventional, naturally occurring amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y). Any of the amino acids in the peptidic molecules forming the present arrays may be replaced by a nonconventional amino acid. Additional information relating to the terms "biomolecule," "nucleotide," and "peptide" can be found in U.S. Patent Application Publication No. 20020037579 to Ellson et al.

The terms "cell" and "cellular" are used herein with their ordinary biological meaning and refer to the smallest structural unit of an organism, living or not, that is capable of independent functioning, and includes one or more of nuclei, cytoplasm, and various organelles, all surrounded by a semipermeable membrane. The term "cellular sample" as used herein refers to a sample that typically contains a plurality of cells. The cells may be of the same type or different types. When the cellular sample contains a single cell, the cell is large, e.g., a fertilized or unfertilized cell. Any number of processing techniques may be used to prepare a cellular sample. For example, the cells may be cultured or extracted from living or dead organisms. In addition, the cellular samples may be prepared for microscopy, e.g., through smears, squashes, mounts, and sections.

The term "fluid" as used herein refers to matter that is nonsolid or at least partially gaseous and/or liquid. A fluid may contain a solid that is minimally, partially, or fully solvated, dispersed, or suspended. Examples of fluids include, without limitation, aqueous liquids (including water per se and salt water) and nonaqueous liquids such as organic solvents and the like. As used herein, the term "fluid" is not synonymous with the term "ink" in that an ink must contain a colorant and may not be gaseous. However, the term "fluid" is intended to encompass fluid inks.

Thus, the term "analysis-enhancing fluid" refers to any fluid that may be required or desired for use in conjunction with an analytical technique. Typically, analysis-enhancing fluids are employed to increase the yield of useful information during surface analysis.

The terms "focusing means" and "acoustic focusing means" refer to a means for causing acoustic waves to converge at a focal point by either a device separate from the acoustic energy source that acts like an optical lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as known in the art and as described, for example, in U.S. Pat. No. 5,798,779 to Nakayasu et al. and Amemiya et al. (1997) *Proceedings of the 1997 IS&TNIP13 International Conference on Digital Printing Technologies*, pp. 698–702.

The term "ion" is used in its conventional sense to refer to a charged atom or molecule, i.e., an atom or molecule that contains an unequal number of protons and electrons. Positive ions contain more protons than electrons, and negative ions contain more electrons than protons. Ordinarily, an ion of the present invention is singly charged, but may in certain instances have a multiple charge.

Accordingly, the term "ionization chamber" as used herein refers to a chamber in which ions are formed from samples—fluid or otherwise—that contain a sample molecule.

The term "moiety" as used herein refers to any particular composition of matter, e.g., a molecular fragment, an intact molecule (including a monomeric molecule, an oligomeric molecule, or a polymer), or a mixture of materials (for example, an alloy or a laminate).

The term "near" as used herein refers to the distance from the focal point of the focused acoustic radiation to the surface of the fluid from which a droplet is to be ejected and indicates that the distance should be such that the focused acoustic radiation directed into the fluid results in droplet ejection from the fluid surface so that one of ordinary skill in the art will be able to select an appropriate distance for any given fluid using straightforward and routine experimentation. Generally, however, a suitable distance between the focal point of the acoustic radiation and the fluid surface is in the range of about 1 to about 15 times the wavelength of the speed of sound in the fluid, more typically in the range of about 1 to about 10 times that wavelength, preferably in the range of about 1 to about 5 times that wavelength.

"Optional" or "optionally" means that the subsequently described circumstance may or may not occur, so that the description includes instances where the circumstance occurs and instances where it does not.

The term "radiation" is used in its ordinary sense and refers to emission and propagation of energy in the form of a waveform disturbance traveling through a medium such that energy is transferred from one particle of the medium to another without causing any permanent displacement of the medium itself. Thus, radiation may refer, for example, to electromagnetic waveforms as well as acoustic vibrations.

The term "reservoir" as used herein refers to a receptacle or chamber for containing a fluid. Thus, a fluid in a reservoir necessarily has a free surface, i.e., a surface that allows a droplet to be ejected therefrom. A reservoir may also be a locus on a substrate surface within which a fluid is constrained or held. In some instances, a reservoir may represent a portion, e.g., a fluid-transporting feature of a microfluidic device.

The term "substantially" as in, for example, the phrase "substantially identical volume," refers to volumes that do not deviate by more than 10%, preferably not more than 5%, more preferably not more than 1%, and most preferably at most 0.1% from each other. Similarly, the phrase "substantially identical reservoirs" refers to reservoirs that do not deviate in acoustic properties. For example, acoustic attenuations of "substantially identical reservoirs" deviate by not more than 10%, preferably not more than 5%, more preferably not more than 1%, and most preferably at most 0.1% from each other. Other uses of the term "substantially" involve an analogous definition.

The term "substrate" as used herein refers to any material having a surface onto which a sample—cellular or otherwise—may be placed and optionally immobilized. The substrate may be constructed in any of a number of forms, for example, wafers, slides, well plates, and membranes. In addition, the substrate may be porous or nonporous as may be required for deposition of a particular fluid. Suitable substrate materials include, but are not limited to, supports that are typically used for solid phase chemical synthesis, for example, polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, and divinylbenzene styrene-based polymers), agarose (e.g., Sepharose®), dextran (e.g., Sephadex®), cellulosic polymers and other polysaccharides, silica and silica-based materials, glass (particularly controlled pore glass (CPG) and functionalized glasses), ceramics, and such substrates treated with surface coatings, such as microporous polymers (particularly cellulosic polymers such as nitrocellulose), microporous metallic compounds (particularly microporous aluminum), antibody-binding proteins (available from Pierce Chemical Co., Rockford, Ill.), bisphenol A polycarbonate, or the like. Additional information relating to the term "substrate" can be found in U.S. Patent Application Publication No. 20020037579 to Ellson et al.

The term "surface modification" as used herein refers to the chemical and/or physical: alteration of a surface by an additive or subtractive process to change one or more chemical and/or physical properties of a surface or a selected site or region of a surface. For example, surface modification may involve (1) changing the wetting properties of a surface, (2) functionalizing a surface, i.e., providing, modifying, or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

The term "tissue" as used herein refers to an aggregation of morphologically similar cells and associated intercellular matter acting together to perform one or more specific functions in a multicellular organism, e.g., a plant or an animal. When the tissue is from an animal, for example, the tissue may be muscle, nerve, epidermal, blood, or connective.

The term "volatility" is used herein in its ordinary sense and refers to the ability of a material to evaporate or become vaporized. For example, a "low volatility" fluid is less easily vaporized than a "high volatility" fluid.

The invention generally provides a method for preparing a sample surface for analysis. The method involves first placing a sample surface in droplet-receiving relationship to a fluid-containing reservoir containing an analysis-enhancing fluid. A droplet of the analysis-enhancing fluid is ejected from the reservoir such that the droplet is deposited on the sample surface at a designated site. Typically, but not necessarily, focused energy, e.g., acoustic energy, is employed to effect droplet ejection. Furthermore, the sample is subjected to conditions sufficient to allow the analysis-enhancing fluid to interact with the sample surface to render the sample surface at the designated site suitable for analysis. Optionally, sufficient energy is applied to the designated site to ionize the sample surface and to release sample molecules therefrom for analysis.

The invention may be used with any sample having a uniform or nonuniform surface of any type. For instance, the sample may be comprised of organic as well as inorganic materials. Examples of inorganic materials include, but are not limited to metals, ceramics, and semiconductors. When the sample is comprised of an organic material, the material may be living, nonliving, or dead.

Nevertheless, cellular samples are particularly suited for use with the invention. Notably, a cellular sample may comprise nearly any type of cell. For example, either or both eukaryotic cells and prokaryotic cells may be used. In some instances, cellular samples are obtained from a mammal. Suitable cell types include, for example, blood cells, stem cells, endothelial cells, epithelial cells, bone cells, liver cells, smooth muscle cells, striated muscle cells, cardiac muscle cells, gastrointestinal cells, nerve cells, and cancer cells. Such cells may be provided as a tissue sample. Alternatively, the cellular sample may comprise cells originating from a cultured cell line or other cell culture.

The cellular sample may be employed in any of a number of forms. The cellular sample is typically nonuniform in composition, and exhibits a substantially planar surface for ease in array formation when a plurality of droplets is deposited on designated sites, as discussed below. In addition, cells are typically immobilized on a substrate surface. Thus, a substrate surface may be selected for facile immobilization of cells. Such surfaces include, for example, a collagen-derivatized surface, dextran, polyacrylamide, nylon, polystyrene, and combinations thereof. In some instances, the surfaces are inherently cytophilic. In other instances, a cytophilic substrate surface is provided as a result of surface modification.

Cells may be immobilized on a substrate surface using conventional techniques known to those skilled in the art. For example, the cells may be immobilized on a cytophilic substrate surface simply by contacting the surface with the cells. In some instances, a centrifuge may be used to produce a force sufficient to immobilize cells in a fluid on a substrate surface. In other instances, cytometers known in the art may be used. In still other instances, acoustic ejection, as described in U.S. Patent Application Publication Nos. 2002/0064808, 2002/0064809, 2002/0094582, and 2002/0090720, may be carried out to place cells on a substrate surface. In addition or in the alternative, the substrate surface may be coated with a layer of a cell-adhering substance, such as collagen, alginate, agar, or other material, to immobilize the cells. When immobilization of cells in a contiguous layer is desired, the cell-adhering substance may be contiguously coated on the target region. When it is desirable to provide an immobilized array of cells, however, the cell-adhering substance may be present as an array of features on a substrate surface. That is, an array of locations on a substrate surface may be coated with an appropriate material to form an array (e.g., patterns such as lanes, checkerboards, spots, or others) so that cells may be spatially arranged at specific locations on the substrate surface.

When the cellular sample is a tissue sample, any of the above immobilization methods may be used. In addition, immobilization of tissue samples may be accomplished by first freezing a relatively large section of tissue. Thereafter, a slicing means such as a knife, microtome, or similar sectioning device is used to slice the frozen tissue into sections. Next, a single section of the tissue is placed onto the substrate (e.g., a glass slide), and the section is allowed to "melt" on the substrate. Those skilled in the art will recognize other immobilization techniques that can be used as well.

In addition, the invention may involve the ejection of fluids of virtually any type and amount desired. The fluids may be aqueous and/or nonaqueous. Examples of fluids include, but are not limited to, aqueous fluids (including water per se and water-solvated ionic and non-ionic solutions, organic solvents, and lipidic liquids); suspensions of immiscible fluids; and suspensions or slurries of solids in liquids. Thus, the fluid may contain, for example, biomolecules such as peptides or nucleotides, enzymes, and/or cellular matter such as whole cells and cell extracts. Commonly, the fluid is selected to preferentially interact with selected moieties on the compositionally nonuniform sample surface. For example, if peptidic digestion is desired, then trypsin, pepsin, or other well-known compounds for peptidic digestion may be included in the fluid. When the invention is used for sample analysis, the fluid may be an analysis-enhancing fluid. That is, the analysis-enhancing fluid may be employed to increase yield of useful information during surface analysis. In some instances, the analysis-enhancing fluid comprises an analysis-enhancing moiety and a carrier fluid. For example, the analysis-enhancing moiety may be a label moiety that is fluorescently, magnetically, or radioactively detectable. The carrier fluid in such cases may include, for example, combinations of water, acetonitrile, alcohols such as ethanol, and ketones such as acetone.

The invention is particularly suited for instances in which a plurality of droplets of one or more analysis-enhancing fluids is deposited on the sample surface. In some instances, the plurality of droplets is deposited on the sample surface at the same designated site. This technique provides control over the formation of the feature at the designated site. For example, if the droplets deposited at the same designated site contains different moieties, the concentration of the different moieties that form the feature can be controlled. In addition, the deposition of droplets at a designated site may correct for any potential deficiency in the presence of a required fluid at the site.

In addition or in the alternative, one or more droplets of analysis-enhancing fluid may be ejected onto the sample surface at different designated sites. In some instances, the different designated sites form an array. In such a case, because the analysis-enhancing fluid renders the designated sites more amenable for analysis, the analysis of the array would result in the analytical "imaging" of the sample surface, as discussed below.

Focused acoustic ejection enables the preparation of arrays that may have a density substantially higher than that possible using other array preparation techniques, such as capillary microspotting and piezoelectric techniques (e.g., using inkjet printing technology). That is, focused acoustic ejection allows for the preparation of arrays with nearly limitless densities of array elements (i.e., sites). In some instances, the density is in the range of approximately 10 to approximately 250,000 array elements (i.e., sites) per square centimeter of sample, typically in the range of approximately 400 to approximately 100,000 array elements per square centimeter of sample surface. However, it must be emphasized that the present method enables preparation of far higher density arrays as well, i.e., arrays comprised of at least about 1,000,000 array elements per square centimeter of sample surface, or even in the range of about 1,500,000 to 4,000,000 elements per square centimeter of sample surface. Also, the matrix can be precisely applied to a sample spot in increments of one picoliter or less, allowing an unparalleled degree of precision Designated sites may correspond to sample regions of specific analytes. Since different analysis-enhancing fluids may specifically enhance one type of analyte over another, the experimenter could effectively analyze an impure sample. For example, one could deposit two analysis-enhancing fluids on two separate subregions of a single analyte region of a sample, or on two or more regions of the same analyte. A region is an area containing analyte that is not contiguous with an adjacent region. A subregion is an area of analyte within a non-contiguous region.

When an analysis-enhancing fluid is deposited on the sample surface, the sample is typically subjected to conditions effective to allow the analysis-enhancing fluid to interact with the sample surface, rendering the sample surface suitable for analysis. Depending on the type of analysis desired, any of a number of different types of interactions may take place between the analysis-enhancing fluid and the sample surface. Thus, for example, when the analysis-enhancing fluid comprises an analysis-enhancing moiety and a carrier fluid, the carrier fluid may be evaporated from the sample surface, thereby leaving the analysis-enhancing moiety in a concentrated form on the sample surface. That is, evaporation of the carrier fluid may increase the local concentration of the analysis-enhancing moiety to effect interaction between the analysis-enhancing moiety and the sample surface.

Depending on the type of analysis desired, any of a number of different types of interaction may take place between the analysis-enhancing moiety and the sample surface. For example, the analysis-enhancing moiety may be selected to break down or digest the constituents of the sample surface. As another example, the analysis-enhancing moiety may bind with selective moieties on the sample surface, thereby rendering the sample surface suitable for analysis. As a further example, the analysis-enhancing fluid may be solidified on the sample surface.

Once appropriate interaction has taken place, the sample at the designated site may be analyzed. Any of a number of analyses may be carried out for the sample at the designated site or sites. Surface-specific properties may be measured by surface-specific physical techniques and physical techniques that are adapted to surface characterization. Various physical surface characterization techniques include, without limitation, diffractive techniques, spectroscopic techniques, microscopic surface imaging techniques, surface ionization mass spectroscopic techniques, thermal desorption techniques, and ellipsometry. It should be appreciated that these classifications are arbitrarily made for purposes of explication, and some overlap may exist. Thus, for example, the inventive device may incorporate analyzing means such as microscopes, optical detectors, fluorescence detectors, magnetic detectors, radioactivity detectors, and combinations thereof.

The invention is particularly suited for mass spectrometry analysis applications involving laser-assisted ionization and desorption. MALDI is an example of such applications. See Karas et al. (1988), "Laser Desorption Ionization of Proteins with Molecular Masses Exceeding 10,000 Daltons," *Anal. Chem.*, 60:2299–2301. In addition, the invention may be employed in conjunction with a variety of surface-based mass spectrometric techniques other than MALDI. For example, one variant of MALDI, called SELDI, uses affinity capture reagents such as antibodies to collect samples from a complex mixture, which allows in situ purification of the analyte followed by conventional MALDI analysis. In such analytical methods, the invention may be used to apply sufficient energy to the sites to ionize and release the sample molecules from the sample surface for analysis. The energy may be applied, for example, by bombarding the sites with photons (e.g., through use of an optional laser), electrons, and/or ions. Ionization and release of sample molecules may be enhanced through heating, directing focused acoustic energy to, and/or passing an electrical current through, at least one site. Once released, the ions may be directed to a mass analyzer/detector. By collecting such mass spectrometric data for a plurality of sites, a compositional map of the sample surface can be constructed. As discussed above, different regions of a single sample may be co-crystallized or complexed with a variety of matrices to facilitate the ionization of a particular component of interest.

For MALDI or SELDI-type analysis, the analysis-enhancing fluid comprises a mass-spectrometry matrix material. Any of a number of photoabsorbing matrix materials known in the art may be employed, and examples of matrix materials for sample analysis include, but are not limited to, 6-aza-2-thiothymine, caffeic acid, 2,5-dihydroxybenzoic acid, α-cyano-4-hydroxy cinnamic acid, 3-hydroxypicolinic acid, and 2-pyrazinecarboxylic acid, and combinations thereof. A plurality of analysis-enhancing fluids may be applied to an analyte to optimize experimental parameters, such as signal and reproducibility. For example, different sub-regions of a single sample could also be probed with a variety of matrices to enhance a particular component of interest. In addition, certain mass-spectrometry matrix materials are particularly suited for certain types of samples. As examples, 3-hydroxypicolinic acid is commonly used for the analysis of glycoproteins, 2-amino-5-nitropyridine is suited for nucleic acid detection, and 6aza-2-thiothymine may be used to analyze proteins.

As discussed above, the accuracy and reliability of such mass spectrometric techniques require control over the formation of the sample matrix. Thus, to provide control of analyte ionization and desorption, it is preferred that features be formed in a consistent manner. This typically requires the deposition of fluid droplets of substantially identical size on a substrate. For example, if the substrate already contains a matrix material, sample droplets containing the same concentration of analyte moieties and of a substantially identical size may be deposited as an array on the substrate. As another example, if the substrate already contains sample materials, identically sized droplets of one or more matrix materials may be deposited on selected sites to form features that facilitate sample ionization and desorption upon bombardment of laser photons. In either case, the matrix material enables the absorption of laser energy to volatilize and ionize the analyte, while preventing analyte decomposition by absorbing significant amounts of laser energy.

For mass spectrometric analysis using the invention, acoustic ejection is employed to coat either an entire sample surface or only designated sites thereon with a mass-spectrometry matrix material. Either or both of the matrix materials and the analyte may thus be deposited on the substrate surface consistently and homogeneously from site to site. If either the matrix material or the analyte is absent, or is present in an inappropriate quantity at a feature, proper ionization will not take place, thereby resulting in inoperative or suboptimal MALDI performance. For example, when fluids are deposited manually to form features on a substrate or a sample surface, one can expect highly variable signal strengths from the different individual features. In many cases, no signal is detected. Moreover, manual deposition of fluid features does not typically enable the study of substructures in a sample wherein the sample features have a cross-sectional dimension of about 10–20 $\mu$m.

In contrast, the invention provides control over the formation of a feature at a designated site. For example, in the context of mass spectrometry, the invention's ability to eject additional matrix material to designated sites that lack sufficient matrix material provides fine control over the amount of matrix material present at a designated site. In particular, acoustic ejection allows highly reproducible quantities of MALDI matrix material, analyte, or another chemical entity to be deposited on regions of a substrate surface. Acoustic ejection additionally provides control over the formation of the sample/matrix complex on the sample surface. As described in U.S. Patent Application Publication No. 2002/0061258, employment of acoustic ejection to dispense fluids results in consistency of feature shape, droplet directionality, and ejected volume that is unmatched by printing methods generally known in the art. Features containing matrix materials on the order of micrometers can be created. Due to the repeatability and precision in placement of droplets through acoustic ejection, additional matrix material may be added to any desired feature site, e.g., to correct for any potential deficiency in the presence of a required fluid. That is, for any feature site, matrix material may be incrementally deposited to ensure that the amount of matrix material at that feature site is optimized for data acquisition. In addition, because acoustic ejection allows for precise placement of ejected droplets, the location of matrix materials at the designated sites will be known with a higher degree of confidence. As a result, there will be no need for the laser to probe a sample multiple times simply to locate the complex. Increasing the frequency and success of experiments greatly reduces the time for sample analysis, leading to greater sample throughput.

When MALDI-type analysis is carried out at these sites, sufficient energy is applied to the sites to ionize and release the sample molecules from the sample surface for analysis. This may involve bombarding a designated site with photons through the use of an optional laser. As discussed above, different regions of a single sample may be co-crystallized with a variety of matrices to facilitate the ionization of a particular component of interest.

Furthermore, the invention is well suited for mass-spectrometric imaging. Such imaging has been described in detail in U.S. Pat. No. 5,808,300 to Caprioli and in Stoeckli et al. (2001), "Imaging Mass Spectrometry: A New Technology for the Analysis of Protein Expression in Mammalian Tissues," *Nature Medicine* 7(4):493–496. In essence, these references describe the use of MALDI mass spectrometry to generate images of samples according to one or more massto-charge ratios. That is, MALDI mass spectrometry is used to analyze the spatial arrangement of specific molecules within a tissue sample. The analysis involves first preparing a test specimen by coating a thin sample layer with an energy absorbent matrix. Then, the test specimen is probed with a laser beam such that a first designated laser spot on the test specimen releases sample molecules. The test specimen is then moved relative to the laser beam and struck with the laser beam such that subsequent designated laser spots on the test specimen release additional sample molecules. The atomic mass of the released sample molecules are measured and mapped to determine the spatial arrangement of specific molecules within the sample. It should be noted that for such mass spectrometric imaging applications, it is desirable to provide an analysis-enhancing fluid that contains mass-spectrometry matrix material that will co-crystallize with, or form crystals on, a sample surface when deposited in small volumes. By careful application of small volumes, high-resolution maps of the composition of sample surfaces can be generated.

A variety of techniques may be used to deposit small volumes of analysis-enhancing fluid on a sample surface. Typically, the invention provides a device or system that includes a reservoir adapted to contain a fluid, an acoustic ejector, an acoustic ejector positioning means, and a sample positioning means. The acoustic ejector comprises an acoustic radiation generator for generating acoustic radiation and a focusing means for focusing the acoustic radiation that is generated. The ejector positioning means is adapted for positioning the acoustic ejector in acoustic coupling relationship to the reservoir. The sample positioning means is adapted for positioning a sample such that a surface of the sample is in droplet-receiving relationship to the reservoir.

Although there is great flexibility in the construction of a suitable reservoir for the invention, some constructions are more suitable than others. As an initial matter, the material used in the construction of the reservoir should be compatible with the fluids contained therein. Thus, if it is intended that the reservoir contain an organic solvent such as acetonitrile, polymers that dissolve or swell in acetonitrile would be unsuitable for use in forming the reservoirs. For water-based fluids, a number of materials are suitable for the construction of the reservoir; these include, but are not limited to, ceramics such as silicon oxide and aluminum oxide, metals such as stainless steel and platinum, and polymers such as polyester and polytetrafluoroethylene. The reservoir is preferably detachable from the inventive device or system, but this is not a necessity. When more than one reservoir is needed, a well plate may be used to contain fluids that are to be ejected. In such a case, the reservoirs, or wells, of the well plate are preferably substantially acoustically indistinguishable from one another. Also, unless it is intended that the ejector be submerged in the fluid to be ejected, the reservoirs or well plates must have acoustic transmission properties sufficient to allow acoustic radiation from the ejector to be conveyed to the surfaces of the fluids to be ejected. Typically, this involves providing reservoir, or well, bases that are sufficiently thin to allow acoustic radiation to travel therethrough without unacceptable dissipation.

As alluded to above, a plurality of reservoirs may be provided, each containing a different fluid. In such a case, focused acoustic energy may be applied in a manner effective to eject a droplet of fluid from each reservoir such that the droplets from the reservoirs are deposited on the sample surface. The droplets of different fluids may be deposited at a single designated site or at different designated sites.

Many commercially available well plates suitable for use with the invention, e.g., as a single reservoir unit that is comprised of a plurality of reservoirs, and may contain, for example, 96, 384, 1536, and 3456 wells per well plate. Manufacturers of suitable well plates for use with the invention include Coming, Inc. (Corning, N.Y.) and Greiner America, Inc. (Lake Mary, Fla.). The availability of such commercially available well plates, however, does not preclude the manufacture and use of custom-made well plates that contain at least about 10,000 wells, or as many as 100,000 wells or more. In some instances, the reservoirs may represent a portion of a microfluidic device, as discussed below. Microfluidic devices are available from ACLARA BioSciences, Inc. (Mountain View, Calif.), Caliper Technologies Corp. (Mountain View, Calif.), and Fluidigm Corp. (South San Francisco, Calif.). The combined employment of focused acoustic ejection and microfluidic devices is discussed in U.S. Patent Application Publication No. 20020125424 to Ellson et al.

Because of the precision that is possible using the inventive technology, the above-described device or system may be used to eject droplets from a reservoir adapted to contain no more than about 100 nanoliters of fluid, preferably no more than about 10 nanoliters of fluid. In certain cases, the ejector may be adapted to eject a droplet from a reservoir adapted to contain about 1 to about 100 nanoliters of fluid. This is particularly useful when it is desirable to eject droplets having small volumes, e.g., about 50 pL or less. In some instances, the fluid to be ejected may contain rare or expensive biomolecules. In such a case, the volume of the ejected droplet may be no greater than about 10 pL, preferably about 1 picoliter or less (e.g., in the range of about 0.025 pL to about 1 pL), which corresponds to deposited droplet diameters of about 20 m or less.

Figure 2:
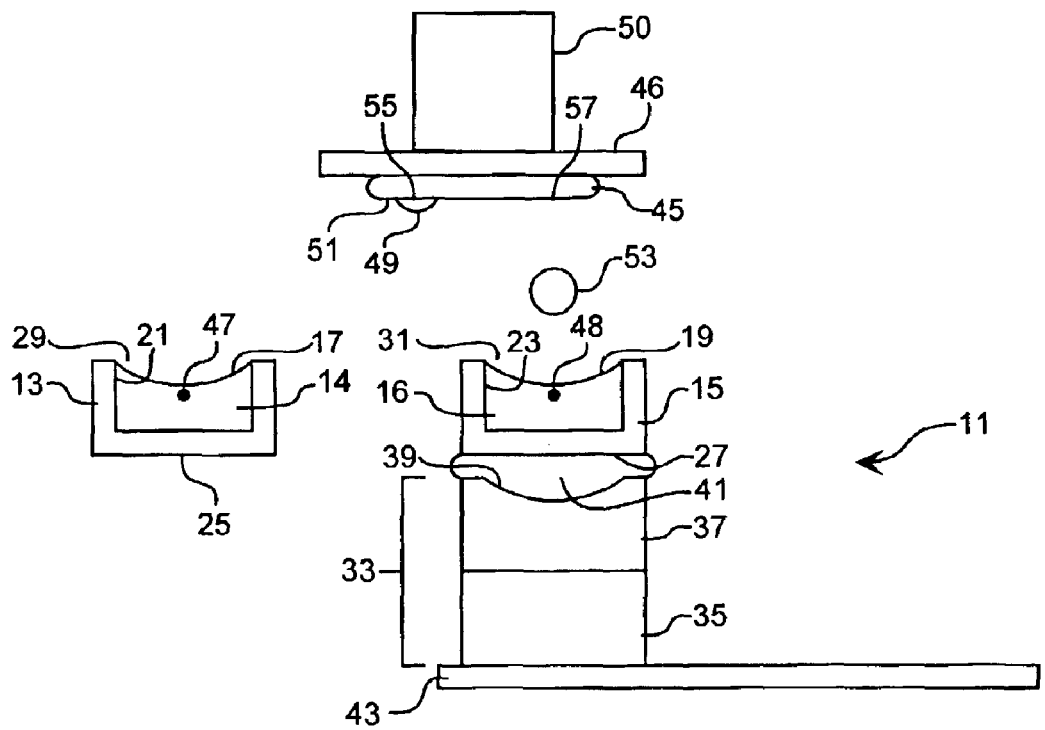
FIG. 2 schematically illustrates the deposition of a second analysis-enhancing fluid on a surface of the tissue sample at a second site.

FIG. 1 illustrates an embodiment of the inventive method for analyzing a cellular sample through mass spectrometry. As with all figures referenced herein, in which like parts are referenced by like numerals, FIG. 1 is not to scale, and certain dimensions may be exaggerated for clarity of presentation. A device for acoustically depositing a fluid on a surface of a cellular sample is depicted in FIGS. 1 and 2. This device is similar in construction to the acoustic ejection device described in U.S. Patent Application Publication No. 2002037579. The device 11 includes a plurality of reservoirs, i.e., at least two reservoirs, although only one reservoir may be required in some instances. A first reservoir is indicated at 13, and a second reservoir is indicated at 15. Each is adapted to contain a fluid having a fluid surface, e.g., a first fluid 14 and a second fluid 16 having fluid surfaces respectively indicated at 17 and 19. Typically, fluids 14 and 16 are different. In order to prepare the sample surface for mass spectrometric analysis, fluids 14 and 16 each comprise a mass-spectrometry matrix material.

The reservoirs are shown in their preferred construction and are substantially identical and acoustically indistinguishable. However, identical construction is not a requirement. In addition, the reservoirs are shown as separate removable components, but they may, if desired, be fixed within a plate or other substrate. For example, the plurality of reservoirs may comprise individual wells in a well plate, optimally although not necessarily, arranged in an array. Each of the reservoirs 13 and 15 is preferably axially symmetric as shown, having vertical walls 21 and 23 extending upward from circular reservoir bases 25 and 27, and terminating at openings 29 and 31, respectively, although other reservoir shapes may be used. The material and thickness of each reservoir base should be such that acoustic radiation may be transmitted therethrough and into the fluid contained within the reservoirs.

The device also includes an acoustic ejector 33, comprised of an acoustic radiation generator 35 for generating acoustic radiation and a focusing means 37 for focusing the acoustic radiation at a focal point within the fluid from which a droplet is to be ejected near the fluid surface. As shown in FIGS. 1 and 2, the focusing means 37 may comprise a single solid piece having a concave surface 39 for focusing acoustic radiation, but the focusing means may be constructed in other ways as discussed below. The acoustic ejector 33 is thus adapted to generate and focus acoustic radiation so as to eject a droplet of fluid from each of the fluid surfaces 17 and 19 when acoustically coupled to reservoirs 13 and 15, and thus to fluids 14 and 16, respectively. The acoustic radiation generator 35 and the focusing means 37 may function as a single unit controlled by a single controller, or they may be independently controlled, depending on the desired performance of the device. Typically, single ejector designs are preferred over multiple ejector designs because accuracy of droplet placement and consistency in droplet size and velocity are more easily achieved with a single ejector. However, the invention is not limited to single ejector designs.

For the present invention, any of a variety of focusing means that include curved surfaces or Fresnel lenses known in the art may be employed in conjunction with the present invention. Such focusing means are described in U.S. Pat. No. 4,308,547 to Lovelady et al. and U.S. Pat. No. 5,041,849 to Quate et al., as well as in U.S. Patent Application Publication No. 2002037579. In addition, there are a number of ways to acoustically couple the ejector to each individual reservoir and thus to the fluid therein. Although acoustic coupling can be achieved through direct contact with the fluid contained in the reservoirs, the preferred approach is to acoustically couple the ejector to the reservoirs and reservoir fluids without allowing any portion of the ejector (e.g., the focusing means) to contact any of the fluids to be ejected. To this end, the present invention provides an ejector positioning means for positioning the ejector in controlled and repeatable acoustic coupling with each of the fluids in the reservoirs to eject droplets therefrom without submerging the ejector therein.

To avoid ejector submersion, direct or indirect contact is typically established between the ejector and the external surface of each reservoir. When direct contact is used in order to acoustically couple the ejector to each reservoir, it is preferred that the direct contact be wholly conformal to ensure efficient acoustic energy transfer. That is, the ejector and the reservoir should have corresponding surfaces adapted for mating contact. Thus, if acoustic coupling is achieved between the ejector and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs that have a specially formed inverse surface.

Optimally, acoustic coupling is achieved between the ejector and each of the reservoirs through indirect contact, as illustrated in FIGS. 1 and 2. In the figures, an acoustic coupling medium 41 is placed between the ejector 33 and the base 25 of reservoir 13, with the ejector and reservoir located at a predetermined distance from each other. The acoustic coupling medium may be an acoustic coupling fluid, preferably an acoustically homogeneous material in conformal contact with both the acoustic focusing means 37 and each reservoir. In addition, it is important to ensure that the fluid medium is substantially free of material having different acoustic properties than the fluid medium itself. As shown, the first reservoir 13 is acoustically coupled to the acoustic focusing means 37 such that an acoustic wave generated by the acoustic radiation generator is directed by the focusing means 37 into the acoustic coupling medium 41, which then transmits the acoustic radiation into the reservoir 13.

In operation, reservoirs 13 and 15 of the device are each filled with first and second fluids 14 and 16, respectively, as shown in FIG. 1. The acoustic ejector 33 is positionable by means of ejector positioning means 43, shown below reservoir 13, in order to achieve acoustic coupling between the ejector and the reservoir through acoustic coupling medium 41. A cellular sample 45 in the form of a tissue section is placed on a substrate 46, which is positioned above and in proximity to the first reservoir 13 such that one surface of the tissue, shown in FIG. 1 as the underside surface 51, faces the reservoir and is substantially parallel to the surface 17 of the fluid 14 therein. Once the ejector, the reservoir, and the tissue sample 45 are in proper alignment, the acoustic radiation generator 35 is activated to produce acoustic radiation that is directed by the focusing means 37 to a focal point 47 near the fluid surface 17 of the first reservoir. As a result, droplet 49 is ejected from the fluid surface 17 onto a designated site 55 on the underside surface 51 of the tissue sample. The ejected droplet may be retained on the tissue surface through adsorption and/or other surface effects. In some instances, the droplet or a nonvolatile portion thereof may be solidified on the tissue surface after contact; in such an embodiment, it may be necessary to maintain the tissue at a low temperature, i.e., a temperature that results in droplet solidification after contact. When droplets are solidified on a tissue surface, it may be desirable to raise all droplets to a temperature sufficient to interact with the tissue surface so as to facilitate analysis.

Then, as shown in FIG. 2, a sample positioning means 50 repositions the cellular sample 45 on the substrate 46 over reservoir 15 in order to receive a droplet therefrom at a second designated site 57. FIG. 2 also shows that the ejector 33 has been repositioned by the ejector positioning means 43 below reservoir 15 and in acoustically coupled relationship thereto by virtue of acoustic coupling medium 41. Once properly aligned as shown in FIG. 2, the acoustic radiation generator 35 of ejector 33 is activated to produce acoustic radiation that is then directed by focusing means 37 to a focal point 48 within the fluid 16 near the fluid surface 19, thereby ejecting droplet 53 onto the cellular sample at the second designated site 57. It should be evident that such operation is illustrative of how the inventive device may be used to eject a plurality of fluids from reservoirs in order to form a pattern, e.g., an array, on the cellular sample surface 51. It should be similarly evident that the device may be adapted to eject a plurality of droplets from one or more reservoirs onto the same site of the cellular sample surface.

It will be appreciated that various components of the device may require individual control or synchronization to form an array on a sample surface. For example, the ejector positioning means may be adapted to eject droplets from each reservoir in a predetermined sequence associated with an array to be prepared on a sample surface. Similarly, the sample positioning means for positioning the sample with respect to the ejector may be adapted to position the sample surface to receive droplets in a pattern or array thereon. Either or both positioning means, i.e., the ejector positioning means and the sample positioning means, may be constructed from, for example, motors, levers, pulleys, gears, a combination thereof, or other electromechanical or mechanical means known to one of ordinary skill in the art. It is preferable to ensure that there is a correspondence between sample movement, ejector movement, and ejector activation to ensure proper array formation.

Figure 3:
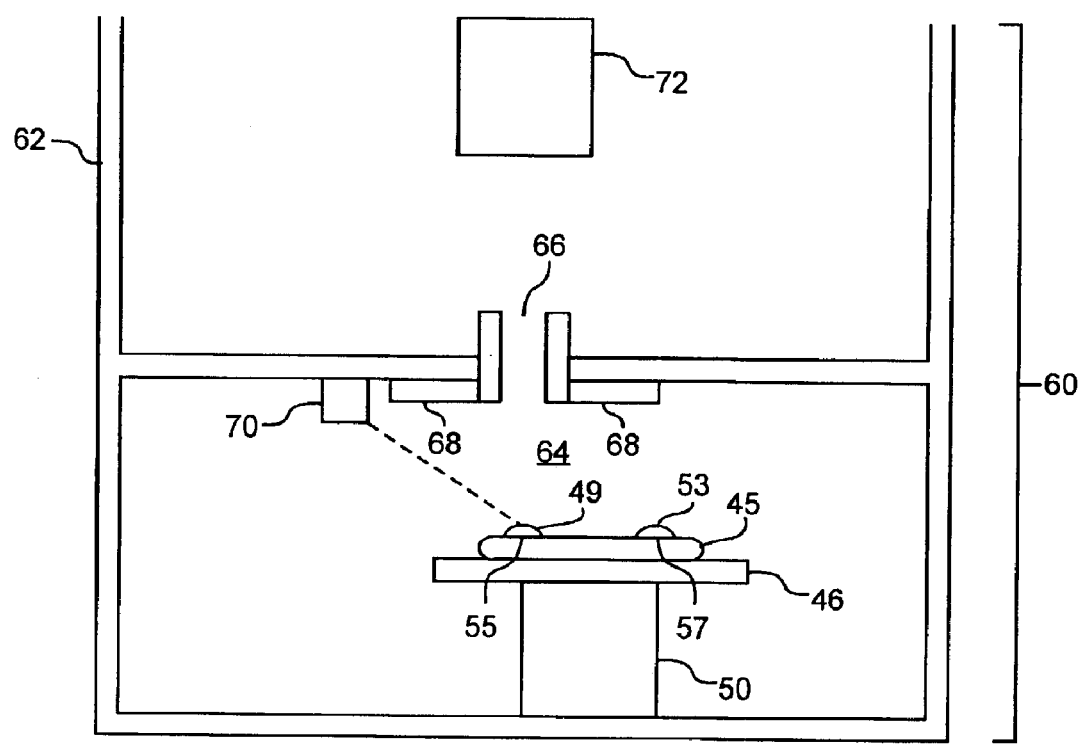
FIG. 3 schematically illustrates the ionization of the tissue sample whose preparation is depicted in FIGS. 1 and 2.

FIG. 3 schematically illustrates an ionization chamber of a mass spectrometer. The ionization chamber 60 comprises a housing 62 containing an ionization region 64, and an interface comprising a capillary 66 and an electrode 68 for attracting ions toward the capillary 66. An energy applying means 70 in the form of a laser and a sample positioning means 50 are provided as well. In operation, the substrate 46 is immobilized with respect to the positioning means 50. As shown, the tissue sample 45 has been subjected to conditions effective to allow the analysis-enhancing fluid droplets 49 and 53 to interact with sample surface 51 so as to render the sample surface suitable for analysis at the designated sites 55 and 57, respectively. The electrode 68 is charged, and once the first designated site 55 and the capillary 66 are in proper alignment, the laser 70 is activated. As a result, ionized sample molecules, formed at the first designated site 55, are released into ionization region 64. The ions are then drawn toward the electrode 68, enter the capillary 66, and are subsequently analyzed by the mass analyzer/detector 72. Examples of such mass analyzers/detectors include multipole detectors, e.g., quadruple detectors, which employ a charged surface that attracts or repels the ionized sample molecule. The identical procedure may be carried out for ionizing sample molecules at the second designated site 57. Additional charged surfaces (not shown) may be placed in the ionization chamber to direct the trajectory of ions.

Thus, it should be evident that the acoustic ejection device illustrated in FIGS. 1 and 2 may share a common registration system with the mass spectrometer illustrated in FIG. 3. This ensures that the sample positioning means for the acoustic ejection device and the mass spectrometer employ the identical sample movement system. In turn, laser irradiation will occur precisely at the designated sites. It should be further evident that these procedures may be controlled using commercially available and/or customized software.

The system illustrated in FIGS. 1–3 provides a number of previously unrealized advantages in the art of mass spectrometry imaging. For example, the invention may be used in the analysis and imaging of peptides and proteins in tumors and other abnormal tissue. With the accuracy and precision associated with acoustic droplet deposition, the analysis may quantify or compare the levels of specific proteins that are more highly expressed in tumors, and/or those that are diminished in expression, relative to normal tissue. Without using acoustic deposition of mass spectrometry matrix materials, accurate location and quantitation of the proteins may not be possible. Furthermore, the invention greatly improves mass spectrometric imaging that may provide a greater understanding of other types of protein expression, e.g., that associated with Parkinson's disease, as well as of drugs and metabolites in tissue.

Furthermore, acoustic deposition increases the spatial resolution of MALDI imaging because the diameter of the fluid droplets deposited can be controlled to approach the diameter of the laser beam used to scan the sample. This diameter is typically about 2 to about 25 $\mu$m. This is important because analysis-enhancing fluids may liberate sample molecules from the sample surface to be analyzed. If droplets exceeding the diameter of the laser focal spot are used, liberated component molecules from different regions of a tissue sample may "mix" and result in cross-contamination. This mixing creates inaccurate or false mass spectrometric images that do not reflect the actual composition of the sample surface. In short, use of excessively large droplets may cause component molecules to migrate and decrease the spatial resolution of the imaging. Since the component molecules within each droplet may be freely transported anywhere within each droplet, droplet size may effectively dictate image resolution.

In addition, the invention also provides a method for selectively depositing an analysis-enhancing fluid on a non-uniform sample surface that exhibits variations in a surface characteristic, wherein the surface characteristic corresponds to desirability for receiving an analysis-enhancing fluid. The surface characteristic corresponding to desirability for receiving analysis-enhancing fluid is typically a compositional or a morphological characteristic. Once a site on the sample surface has been selected according to the surface characteristic at the site, focused radiation, typically acoustic radiation, is applied in a manner effective to eject a droplet of the analysis-enhancing fluid from a reservoir. In some instances, the sample may exhibit variations in a plurality of surface characteristics, wherein each characteristic corresponds to desirability for receiving a different analysis-enhancing fluid. In such a case, droplets of different analysis-enhancing fluids may be deposited on the sample surface at the corresponding selected sites.

Optionally, the sample at the selected site may be analyzed. Typical analytical techniques that benefit from the invention include, but are not limited to, mass spectrometry, structural analysis, and microscopy. In addition, the invention is also particularly suited for use with surface imaging techniques. In some instances, a sample surface is imaged so as to map the variations in a surface characteristic, and one or more sites are selected on the sample surface using the results of the surface imaging. Preferably, surface imaging results in the production of a digital image. Further optionally, the image contrast of the variations in the surface characteristic is increased before the surface is imaged. This may involve, for example, staining the sample surface such that regions exhibiting the desired surface characteristic are more readily resolved by an imaging means.

Typically, though not necessarily, the inventive method may be carried out using a device or system similar to that described above adapted for selectively depositing an analysis-enhancing fluid on a surface of a sample. As discussed above, provided are a reservoir containing an analysis-enhancing fluid, an acoustic ejector comprising an acoustic radiation generator for generating acoustic radiation and a focusing means for focusing the acoustic radiation generated, and a means for positioning the acoustic ejector in acoustic coupling relationship to the reservoir. Also provided is a means for selecting at least one site on the sample surface for deposition of analysis-enhancing fluid thereon. Site selection is carried out according to a surface characteristic that corresponds to desirability for receiving the analysis-enhancing fluid. The system also includes a means for positioning the sample such that the selected site or sites are positioned in droplet-receiving relationship to the reservoir. The sample positioning means may be adapted to controllably position the sample such that when a plurality of sites on the sample surface is selected, the selected sites are successively placed in droplet-receiving relationship to the reservoir. Optionally, a means for analyzing the composition of the sample at the selected site may also be provided.

Figure 4:
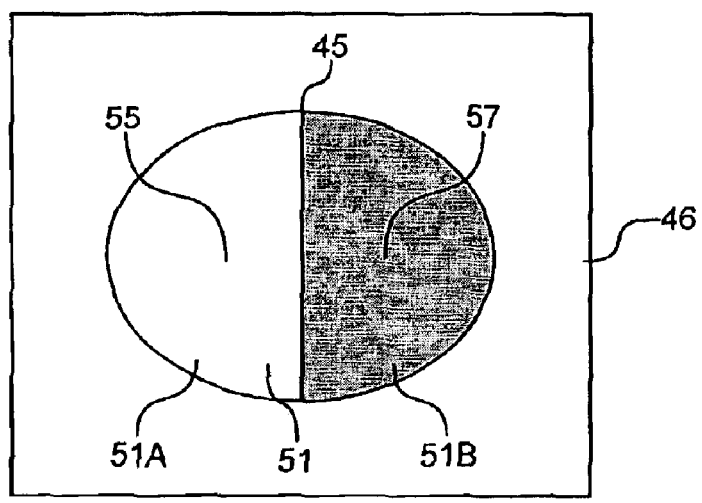
FIG. 4 schematically illustrates in top view a tissue sample on a substrate, wherein the tissue sample exhibits a nonuniform exposed surface.

FIGS. 4–8 illustrate an embodiment of the inventive method for selectively depositing and analyzing a cellular sample through mass spectrometry. FIG. 4 illustrates an exemplary cellular sample 45 placed on a substrate 46 for use with the invention. As depicted, the sample 45 is a tissue sample having a substantially planar and nonuniform surface 51. As shown, the surface 51 includes two distinct regions, the first region 51A depicted without shading, and the second region 51B, depicted with shading. Region 51A exhibits a first surface characteristic that corresponds to desirability for receiving a first analysis-enhancing fluid 14 (shown in FIGS. 3 and 4), and region 51B exhibits a second surface characteristic that corresponds to desirability for receiving a second analysis-enhancing fluid 16 (shown in FIGS. 3 and 4).

Figure 5:
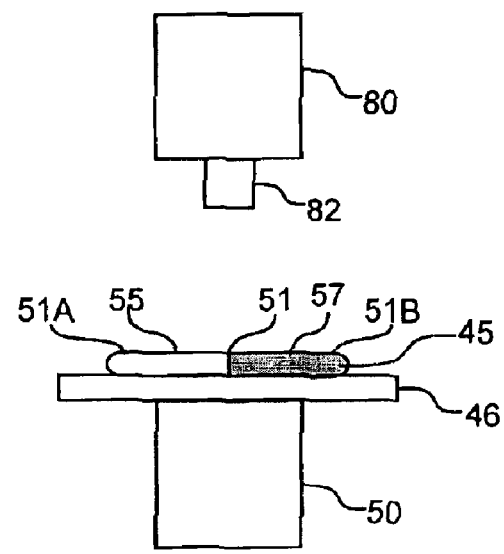
FIG. 5 schematically illustrates in side view the imaging of the exposed surface of the tissue sample depicted in FIG. 4.

In order to select sites on the sample according to desirability for receiving analysis-enhancing fluid, it may be necessary to image the sample surface. As shown in FIG. 5, a combination unit 80 is provided that serves as a selecting means and a controller. The combination unit includes an imaging means 82 adapted to produce a digital image of the sample surface 51. The digital image of the sample surface captured by the imaging means 82 is stored and optionally analyzed in the combination unit 80. As a result, one or more sites on the sample surface 51 may be selected according to the surface characteristics at the site or sites. This selection data, in turn, may be used in a system to selectively deposit fluids onto the sample surface at the sites. As depicted, once an image of the sample surface 51 is obtained, the combination unit, acting as a selecting means, will determine that site 55 in region 51A is desirable for receiving the first analysis-enhancing fluid 14 and site 57 in region 51B is desirable for receiving the second analysis-enhancing fluid 16.

Figure 6:
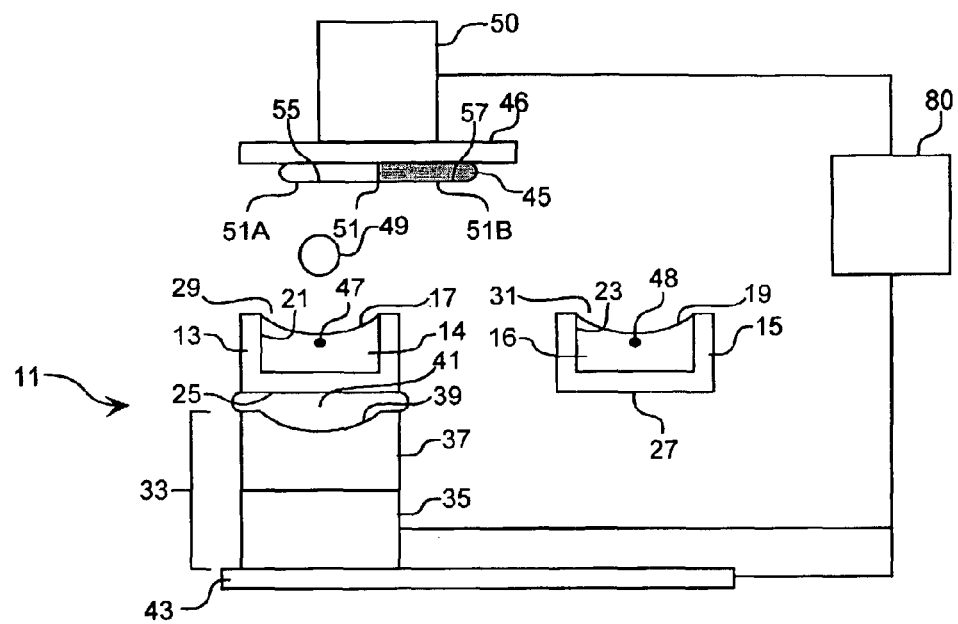
FIG. 6 schematically illustrates in side view the deposition of a first analysis-enhancing fluid on a surface of the tissue sample depicted in FIG. 4 at a first site selected according to a first surface characteristic.
Figure 7:
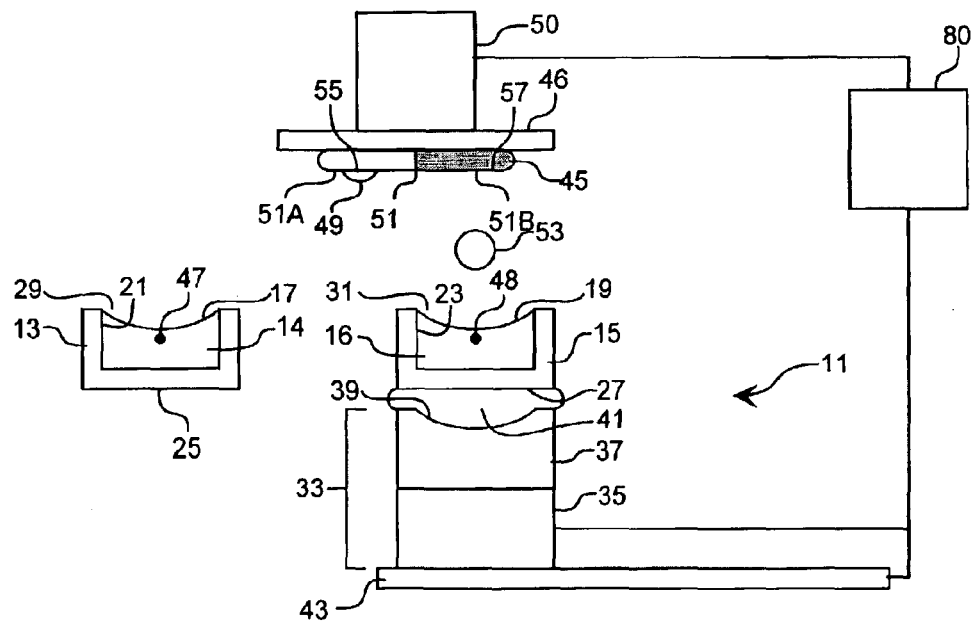
FIG. 7 schematically illustrates in side view the deposition of a second analysis-enhancing fluid on a surface of the tissue sample depicted in FIG. 4 at a second site selected according to a second surface characteristic.

An exemplary device for acoustically depositing a fluid on a surface of a cellular sample is shown in FIGS. 6 and 7. The device is similar in construction to the acoustic ejection device depicted in FIGS. 1 and 2 described in U.S. Patent Application Publication No. 20020037579 to Ellson et al. As surface characteristics of regions 51A and 51B are different, fluids 14 and 16, selected for deposition on regions 51A and 51B, respectively, are different as well. In order to prepare the sample surface for mass spectrometric analysis, fluids 14 and 16 each comprise a mass spectrometry matrix material.

In operation, reservoirs 13 and 15 of the device are each filled with first and second analysis-enhancing fluids 14 and 16, respectively, as shown in FIG. 6. The combination unit 80 is provided to achieve correspondence between sample movement, ejector movement, and ejector activation. The ejector positioning means 43 positions the acoustic ejector 33 below reservoir 13 and to achieve acoustic coupling between the ejector and the reservoir through acoustic coupling medium 41. Cellular sample 45 is positioned by sample positioning means 50 above and in proximity to the first reservoir 13 such that the exposed surface 51 of the tissue faces the reservoir and is substantially parallel to the surface 17 of the fluid 14 therein. Site 55 in region 51A is placed in position to receive a droplet of the first analysis-enhancing fluid 14 from reservoir 13. Once the ejector, the reservoir, and the tissue sample 45 are in proper alignment, the combination unit 80 activates acoustic radiation generator 35 to produce acoustic radiation. The focusing means 37 directs the generated acoustic radiation to a focal point 47 near the fluid surface 17 of the first reservoir. As a result, droplet 49 is ejected from the fluid surface 17 onto the first selected site 55 on surface 51 of the tissue sample.

Figure 8:
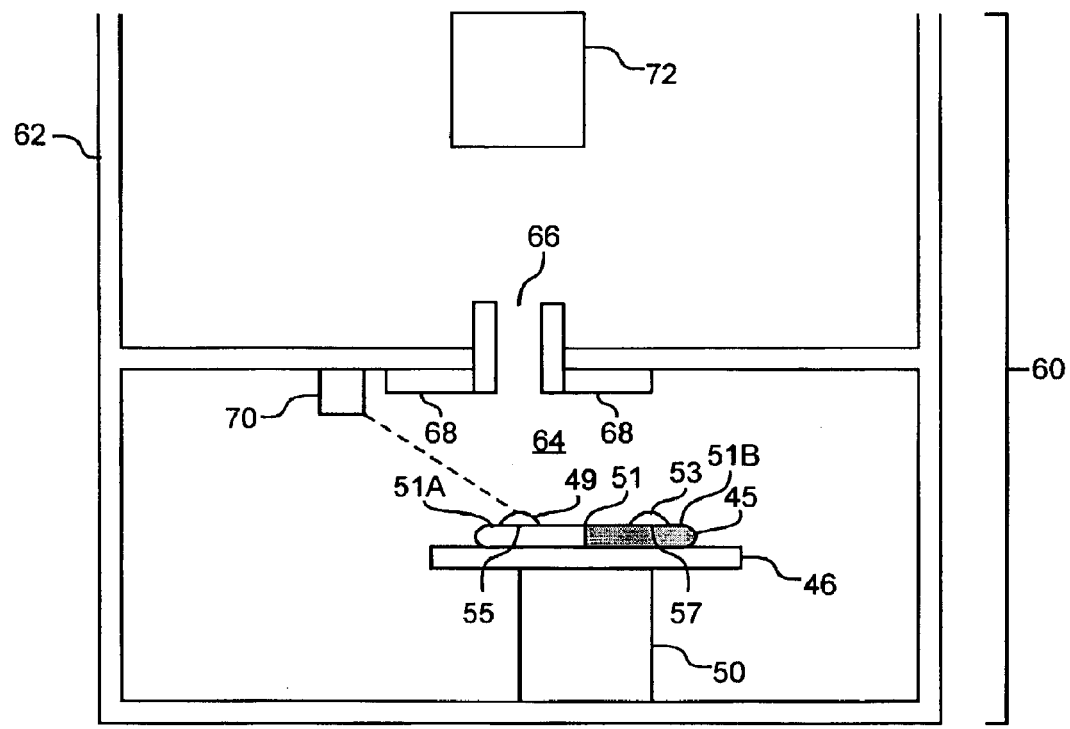
FIG. 8 schematically illustrates in side view the ionization of the tissue sample whose preparation is depicted in FIGS. 6 and 7.

Then, as shown in FIG. 7, a sample positioning means 50 repositions the cellular sample 45 on the substrate 46 over reservoir 15 in order to receive a droplet therefrom at the second selected site 57. In addition, the ejector 33 has been repositioned by the ejector positioning means 43 below reservoir 15 and in acoustically coupled relationship thereto by virtue of acoustic coupling medium 41. With proper alignment droplet 53 is ejected onto the cellular sample at the second selected site 57. FIG. 8 schematically illustrates the ionization chamber of FIG. 3 as adapted for use with the sample prepared using the device depicted in FIGS. 6 and 7. The mass ionization chamber may also employ a common registration system with the acoustic ejection device illustrated in FIGS. 6 and 7 and the mass spectrometer illustrated in FIG. 5.

The surface characteristic corresponding to desirability for receiving analysis-enhancing fluid is typically a compositional or morphological characteristic. Such characteristics may be optically and/or acoustically detectable. The detectability may optionally be enhanced by staining or through the use of acoustic contrast enhancement fluids.

Thus, in some embodiments, the inventive system may include a selecting means comprised of a means for imaging the sample surface so as to map the variations in the surface characteristic, and a means for selecting at least one site on the sample surface using the results produced by the imaging means. The imaging means is typically adapted to produce a digital image and may, for example, employ a scanner or a camera. In other instances, an image of the sample surface that maps the variations in the surface characteristic is produced without an imaging means. In either case, the selecting means may select sites for analysis-enhancing fluid deposition when the surface characteristic is above a threshold level and/or when the surface characteristic is within a predetermined range. The selecting means may employ imaging technologies known in the art. A variety of imaging software, firmware, and hardware are commercially available, as well as microscopes and other image magnification devices suitable for providing more detailed resolution of surface inhomogeneities. Optionally, the image contrast of the variations in the surface characteristic is increased before the surface is imaged. This may involve, for example, staining or labeling the sample surface such that regions exhibiting the desired surface characteristic are more readily resolved by an imaging means.

In some instances, the sample may exhibit variations in a plurality of surface characteristics, wherein each characteristic corresponds to desirability for receiving a different analysis-enhancing fluid. In such a case, droplets of different analysis-enhancing fluids may be deposited on the sample surface at the corresponding selected sites. In addition, different analysis-enhancing fluids may be deposited on the sample surface at the same site. In some instance, droplets of a first analysis-enhancing fluid may be sparsely deposited on an array of surface sites so as to survey the surface and to provide a "big picture" overview of the surface characteristics of interest. From the "big picture" overview, one may determine whether and optionally how to deposit additional droplets of the same and/or different analysis-enhancing fluid to form a high-density array of on the sample surface.

The analysis-enhancing fluid may be selected according to the type of analysis desired, preferably to increase the yield of useful information during surface analysis. In some instances, the analysis-enhancing fluid comprises a label moiety, such as one or more selected from the group consisting of a fluorescent moiety, a magnetic moiety, and a radioactive moiety. However, it should be noted that label moieties do not have to be employed in conjunction with the analysis-enhancing fluid; such label moieties may be used separately from the use of analysis-enhancing fluid. In addition or in the alternative, the analysis-enhancing fluid may contain biomolecules (such as peptides or nucleotides) and/or cellular matter (such as whole cells and cell extracts).

Often, the analysis-enhancing fluid is selected to preferentially interact with selected moieties on a compositionally nonuniform sample surface. For example, if peptidic digestion is desired, then trypsin, pepsin, or other well-known compounds for peptidic digestion may be included in the fluid. Thus, an enzymatic biomolecule such as a protease is provided to enhance breakdown of the corresponding substrate moiety on or near the sample surface.

In addition, the analysis-enhancing fluid may comprise an analysis-enhancing moiety and a carrier fluid. The carrier fluid in such cases may include, for example, combinations of water, acetonitrile, alcohols (such as ethanol), and ketones (such as acetone). Thus, it should be apparent that the invention may involve the ejection of fluids of virtually any type and amount desired, including fluids that do not enhance analysis, although at least one analysis-enhancing fluid is typically used. The fluids may be aqueous and/or nonaqueous. Examples of fluids include, but are not limited to, aqueous fluids (including water per se and water-solvated ionic and nonionic solutions, organic solvents, and lipidic liquids), suspensions of immiscible fluids, and suspensions or slurries of solids in liquids. Evaporation of the carrier fluid increases the local concentration of the analysis-enhancing moiety to effect interaction between the analysis-enhancing moiety and the substrate surface. Depending on the type of analysis desired, any of a number of different types of interaction might take place between the analysis-enhancing moiety and the sample surface. For example, the analysis-enhancing moiety may be selected to break down or digest the constituents of the sample surface. As another example, the analysis-enhancing moiety may bind with selective moieties on the sample surface, thereby rendering the substrate surface suitable for analysis. Thus, analysis-enhancing fluids may enhance the suitability of a sample to be analyzed by modifying the sample surface.

Means other than mass spectrometry for analyzing the sample may be provided as well. Such analyzing means may include, for example, an optical detector, a radiation detector, and/or a magnetic detector. In some instances, the invention may be used to enhance analysis of inorganic material. One example in which this may be carried out is to selectively deposit a particular etchant on an alloy surface to etch a particular phase of the alloy. As another example, the invention may enhance strain analysis. For instance, U.S. Pat. No. 6,327,030 to Ifju et al. describes a method for measuring strain on a substrate material. The method involves preparing the substrate material for strain measurement by applying a luminescent coating to a substrate material, curing the coating, and illuminating the coating with excitation illumination. Then, characteristics of luminescent light emanating from the coating are measured in order to determine strain on the substrate material. The characteristics of luminescent light emanating from the coating are related to strain on the substrate material due, at least in part, to a relationship between the amount of strain on the substrate material and the morphology of cracks in the coating. The present invention provides a convenient technique to improve such a strain measurement method. Since it is known that some materials exhibit preferential strain proliferation when they possess certain morphological characteristics, e.g., surface scratches and texturing, the coating may be selectively applied only to regions on the substrate that exhibit such morphological characteristics for analysis. In this way, excess coating is not wasted through its application to regions where such characteristics are absent.

Figure 9:
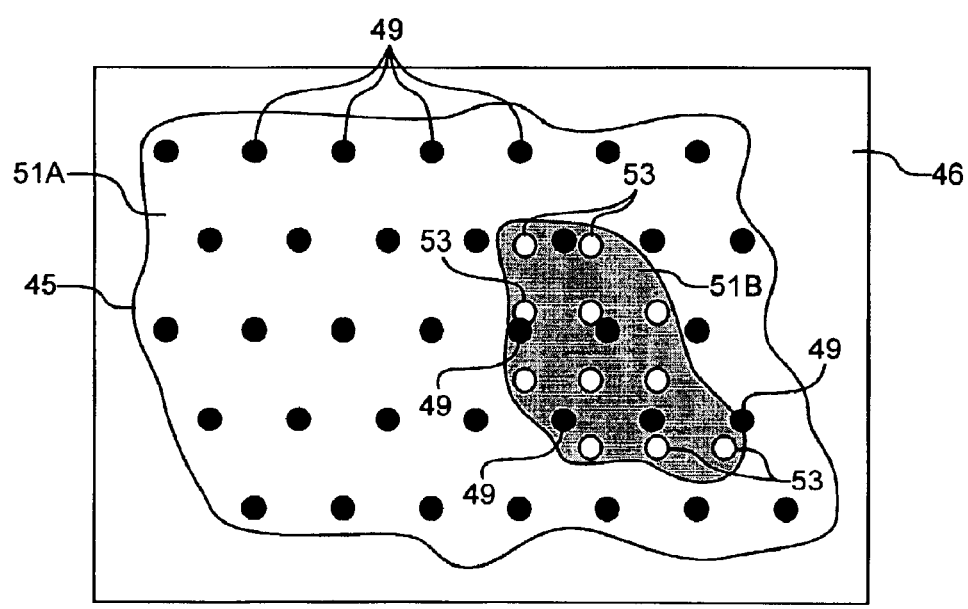
FIG. 9 schematically illustrates in top view a tissue sample exhibiting a nonuniform upper surface having droplets of different analysis-enhancing fluids deposited thereon at different sites. These sites are selected according to specific surface characteristics, and the sites associated with each analysis-enhancing fluid form an array.

It should be noted that the invention may be advantageously used in combination with surface mapping technologies, such as those described in U.S. Pat. No. 5,808,300 to Caprioli and in U.S. Patent Application Publication No. 2002/0171037 to Ellson et al. For example, FIG. 9 schematically depicts tissue sample 45 on a substrate 46. The exposed sample surface 51 is nonuniform. As shown, the surface 51 is comprised of a first region 51A circumscribing a second region 51B. The first region 51A may be, for example, comprised of lean tissue and the second region 51B comprised of lipid tissue. In such a situation, it may be desirable to place an analysis-enhancing fluid on only one of the regions. That is, the sites for fluid deposition may be selected according to lipid and/or peptide content at the site. As lipid tissue and lean tissue are typically optically distinguishable from one another, fluid deposition in this instance would involve selecting sites on the surface according to the optical characteristics displayed (i.e., at the sites associated with either lipid or lean tissue).

The invention provides a method that combines the mapping technologies as discussed above with the advantages of enhancement of analysis at a selected region. An example of such combined use is depicted in FIG. 9, wherein droplets of a first analysis-enhancing fluid, indicated at 49, are deposited at a first array of sites on the sample surface 51, and droplets of a second analysis-enhancing fluid, indicated at 53, are deposited at a second array of sites on the sample surface 51. The first fluid enhances peptide analysis while the second fluid enhances lipid analysis. The first fluid is deposited in both regions 51A and 51B, while the second fluid is deposited only within region 51B. Thus, by analyzing the sample at each site having the first fluid deposited thereon, a map of peptide composition of the overall sample surface can be constructed. Similarly, by analyzing the sample at each site having the second fluid deposited thereon, the lipidic region 51B may be selectively analyzed.

As discussed above, the invention may involve the use of analyte-enhancing fluids, such as those containing a mass-spectrometry matrix material dissolved in a solvent. When such a solution is ejected from a reservoir toward a sample surface, the solution should contact the surface and be subjected to conditions sufficient for the matrix material to interact with and/or co-crystallize with the sample surface to render the sample surface suitable for analysis.

One factor that determines the quality of matrix crystals is the rate of evaporation of the solvent from a mass-spectrometry matrix solution. Given various volumes of fluid solutions having the same shape, the solvent evaporation rates for smaller fluid volumes are faster than for larger fluid volumes, because the surface-to-volume ratio increases as fluid volume decreases. For example, a spherical droplet having a 20 $\mu$m diameter will have five times the surface-to-volume ratio of a droplet having a 100 $\mu$m diameter. Accordingly, the smaller droplet would lose a greater fraction of its total volume per unit time than the larger droplet.

Typically, one of ordinary skill in the art would select a highly volatile solvent for use with a mass-spectrometry matrix to form a mass-spectrometry analysis-enhancing fluid so as to facilitate rapid evaporation of the solvent and co-crystallization of the matrix material with the sample surface. Similarly, low volatility solvents such as dimethylsulfoxide (DMSO) and glycerol are avoided in MALDI-TOF applications. It has recently been discovered that when small-volume droplets containing a mass-spectrometry matrix material dissolved in a highly volatile solvent are ejected from a reservoir, the matrix material may not co-crystallize properly with the sample surface. In extreme cases, the matrix material will not co-crystallize at all with the sample surface. For example, a typical MALDI matrix solution for the study of protein samples contains a 1:1 mixture of water and acetonitrile containing 0.2% trifluoroacetic acid. The solution contains sinapinic acid at a near saturation concentration of 40 mg/mL. When such a solution was spotted onto a typical gold substrate containing a tissue sample at volumes of 30 picoliters or less, the signal was not adequate for protein identification. Therefore, it is likely that an inadequate amount of sample was co-crystallized with the matrix to allow signal acquisition, and that the amount of deposited matrix was inadequate. It is further likely that these co-crystallization problems were caused by excessive evaporation of the solvent while the droplets were traveling from the reservoir to the sample surface. Even when droplets containing a highly volatile solvent contact the surface, such droplets may not have sufficient time to penetrate and interact with the surface before the solvent evaporates. Thus, the invention also provides for methods and techniques to slow evaporation rates for small droplets of mass-spectrometric matrix solutions so as to allow adequate analyte co-solvation and crystallization.

In this regard, the invention also provides for a method for preparing a sample surface for analysis that involves the use of an analysis-enhancing fluid comprising an analysis-enhancing moiety and a carrier fluid, wherein the carrier fluid is comprised of a low volatility solvent that has a boiling point greater than 100° C. at a pressure of 1 atmosphere. A sample is placed such that a surface thereof is in droplet-receiving relationship to a reservoir containing the analyte-enhancing fluid. Once a droplet of the analysis-enhancing fluid is ejected from the reservoir and deposited on the sample surface at a designated site, the sample is subjected to conditions sufficient to allow the analysis-enhancing fluid to interact with the sample surface to render the sample surface suitable for analysis. A low volatility solvent is employed to ensure that the analysis-enhancing moiety, e.g., a mass-spectrometry matrix material, remains sufficiently solvated by the solvent so as to retain its ability to interact with the sample surface, so as to be suitable for analysis. As solvent volatility is generally correlated to its ability to slow the overall evaporation rate of a droplet of fluid, solvents lower in volatility may be selected for droplets lower in volume. For example, solvents having boiling points of at least 120° C., 150° C., and 180° C. at a pressure of 1 atmosphere may be selected for droplets of decreasing lower volumes. Exemplary solvents having low volatility include, but are not limited to, dimethylsulfoxide (DMSO), glycerol, propylene carbonate, valeronitrile, malononitrile, sulfolane, 3-methylsulfolane, and higher alcohols and ketones.

Optionally, the carrier fluid may comprise a mixture of high and low volatility solvents. The proportion of the solvents may be selected according the desired performance. For mass spectrometry analysis described herein using acoustic ejection, the carrier fluid typically contains the high volatility solvent at a higher concentration than the low volatility solvent. Preferably, the carrier fluid contains at least about 75% of the low volatility solvent. More preferably, the carrier fluid contains at least about 90% of the low volatility solvent. Optimally, the carrier fluid contains at least about 98% of the low volatility solvent.

In addition, other techniques may be used to control the evaporation of the solvent. For example, in order to accelerate the evaporation of a low volatility solvent on a sample surface, one may subject the sample to a higher temperature and/or a lower pressure. For samples kept under ordinary laboratory conditions, this may involve subjecting the sample to a temperature greater than 25° C. or a pressure lower than about 1 atmosphere. Similarly, one may subject a sample to a lower temperature and/or higher pressure to hinder evaporation of a high volatility solvent on a sample surface. For samples kept under ordinary laboratory conditions, this may involve subjecting the sample to a temperature of less than 25° C. and/or a pressure greater than 1 atmosphere. Thus, it should be apparent to those of ordinary skill in the art that control over solvent evaporation relates to the partial pressure of the solvent. In order to ensure that a solvent does not evaporate too quickly, a sample having an analysis-enhancing fluid comprised of a mass spectrometry matrix material and the solvent may be subjected to an atmosphere that is at least about 30% saturated with the carrier fluid to allow the analysis-enhancing fluid to interact with the sample surface and to render the sample surface suitable for analysis. To slow evaporation of the solvent further, the atmosphere may be at least about 50%, 75%, or 90% saturated with the carrier fluid.

Those of ordinary skill in the art will also recognize that the volatility of a fluid is a relative measure that depends on both the composition of the fluid and the environment to which the fluid is exposed. In general, water at 25° C. in an overall environment pressure of 1 atmosphere (760 mm/Hg) may sometimes be considered a fluid of neither high nor low volatility. The saturated vapor pressure for water in such an environment is about 23.76 mm/Hg. If one defines that the volatility quotient of the a fluid as the ratio of the environmental pressure to the saturated vapor pressure the fluid, the volatility quotient for water in such an environment is about 30. Using this water as a reference fluid, then, a high volatility fluid would have volatility quotient less than about 30 and a low volatility fluid would have a volatility quotient greater than about 30. For the present invention, a variety of volatility quotients are suitable, e.g., 30, 50, 75, 100.

Variations of the present invention will be apparent to those of ordinary skill in the art. For instance, one of ordinary skill in the art would recognize that the volatility of a fluid mixture may change over time as more volatile components escape from the mixture. The skilled artisan will also recognize that Rayleigh's Law may apply to such mixtures. For example, a droplet comprised of 50% water, 48% acetonitrile, and 2% DMSO will have a higher initial vapor pressure than a droplet comprised of pure water. As acetonitrile is volatilized from such a droplet, the DMSO concentration will rise, and the droplet may eventually have a lower vapor pressure than a droplet comprised of pure water. Ultimately, the equilibrium fluid concentration of the droplet will be 30% water and 70% DMSO, depending on the relative humidity of the atmosphere in contact with the sample surface It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

We claim:

1. A method for preparing a sample surface for analysis, comprising:
   (a) providing a reservoir containing an analysis-enhancing fluid, wherein the analysis-enhancing fluid is comprised of an analysis-enhancing moiety and a carrier fluid, and the carrier fluid is comprised of a low volatility solvent that has a boiling point greater than 100° C. at a pressure of 1 atmosphere;

(b) placing a surface of a sample in droplet-receiving relationship to the fluid-containing reservoir;

(c) applying focused acoustic energy in a manner effective to eject a droplet of the analysis-enhancing fluid from the reservoir such that the droplet is deposited on the sample surface at a designated site; and (d) subjecting the sample to conditions sufficient to allow the analysis-enhancing fluid to interact with the sample surface to render the sample surface suitable for analysis.

2. The method of claim 1, wherein the carrier fluid further comprises a high volatility solvent that has a boiling point less than 100° C. at a pressure of 1 atmosphere.

3. The method of claim 2, wherein the carrier fluid contains the high volatility solvent at a higher concentration than the low volatility solvent.

4. The method of claim 1, wherein the analysis-enhancing moiety comprises a mass spectrometry matrix material.

5. The method of claim 4, wherein the mass spectrometry matrix material is a photoabsorbing matrix material.

6. The method of claim 1, wherein the analysis-enhancing fluid comprises a label moiety.

7. The method of claim 1, wherein the analysis-enhancing fluid comprises a biomolecule.

8. The method of claim 1, wherein the low volatility solvent has a boiling point greater than 120° C. at a pressure of 1 atmosphere.

9. The method of claim 8, wherein the low volatility solvent has a boiling point greater than 150° C. at a pressure of 1 atmosphere.

10. The method of claim 9, wherein the low volatility solvent has a boiling point greater than about 180° C. at a pressure of 1 atmosphere.

11. The method of claim 1, wherein the sample is a cellular sample.

12. The method of claim 11, wherein the cellular sample is selected from a tissue sample, a cell culture, a single cell, or a plurality of cells immobilized on a substrate surface.

13. The method of claim 1, wherein the sample surface is substantially planar.

14. The method of claim 1, wherein step (c) is repeated such that a plurality of droplets is deposited on the sample surface.

15. The method of claim 14, wherein the plurality of droplets is deposited on the sample surface at the same designated site.

16. The method of claim 14, wherein the plurality of droplets is deposited on the sample surface at different designated sites.

17. The method of claim 16, wherein the different designated sites form an array.

18. The method of claim 1, wherein the sample surface exhibits variations in a surface characteristic that correspond to desirability for receiving an analysis-enhancing fluid, and the designated site is selected according to the surface characteristic at the site.

19. The method of claim 18, wherein the surface characteristic is a compositional and/or morphological characteristic.

20. The method of claim 18, wherein the surface characteristic is optically and/or acoustically detectable.

21. The method of claim 1, wherein step (a) comprises providing a plurality of reservoirs, each containing a different analysis-enhancing fluid, and step (c) comprises applying focused acoustic energy in a manner effective to eject a droplet of fluid from each reservoir such that the droplets from the reservoirs are deposited on at least one designated site on the sample surface.

22. The method of claim 21, wherein droplets of different analysis-enhancing fluids are deposited on the sample surface at the same designated site.

23. The method of claim 21, wherein the droplets are deposited on the sample surface at different designated sites.

24. The method of claim 23, wherein the different designated sites form an array.

25. The method of claim 23, wherein the different designated sites are selected according to variations in a surface characteristic of the sample.

26. The method of claim 1, further comprising, after step (d), (e) analyzing the sample at the selected site.

27. The method of claim 26, further comprising, after step (d) and before step (e), (d') applying effective energy to the designated site to release sample molecules from the sample surface for analysis.

28. The method of claim 27, wherein step (d') comprises bombarding the designated site with photons, electrons, ions, or combinations thereof.

29. The method of claim 27, wherein step (d') comprises heating, directing focused acoustic energy to, and/or passing an electrical current through the designated site.

30. The method of claim 26, wherein step (e) comprises performing mass spectrometric analysis on the sample molecules.

31. A method for preparing a sample surface for analysis, comprising:

(a) providing a reservoir containing an analysis-enhancing fluid, wherein the analysis-enhancing fluid is comprised of an analysis-enhancing moiety and a carrier fluid, and the carrier fluid is comprised of a low volatility solvent that has a boiling point greater than 100° C. at a pressure of 1 atmosphere;

(b) placing a surface of a sample in droplet-receiving relationship to the fluid-containing reservoir;

(c) ejecting a droplet of the analysis-enhancing fluid from the reservoir such that the droplet is deposited on the sample surface at a designated site, wherein the ejected droplet has a volume of no greater than about 50 pL; and (d) subjecting the sample to conditions sufficient to allow the analysis-enhancing fluid to interact with the sample surface to render the sample surface suitable for analysis.

32. The method of claim 31, wherein the volume of the ejected droplet is no greater than about 10 pL.

33. The method of claim 32, wherein the volume of the ejected droplet is no greater than about 1 pL.

34. The method of claim 33, wherein the volume of the ejected droplet is in the range of about 0.025 pL to about 1 pL.

35. The method of claim 31, wherein step (c) is carried out by applying focused acoustic energy to the analysis-enhancing fluid contained in the reservoir in a manner effective to eject a droplet therefrom.

36. The method of claim 35, further comprising, after step (d), (e) analyzing the sample at the selected site.

37. The method of claim 36, further comprising, after step (d) and before step (e), (d') applying effective energy to the designated site to release sample molecules from the sample surface for analysis.

38. The method of claim 37, wherein step (d') comprises bombarding the designated site with photons, electrons, ions, or combinations thereof.

39. The method of claim 36, wherein step (e) comprises performing mass spectrometric analysis on the sample molecules.

40. The method of claim 36, wherein the sample is a cellular sample.

41. A method for preparing a sample surface for mass spectrometry analysis, comprising:
   (a) providing a reservoir containing an analysis-enhancing fluid, wherein the analysis-enhancing fluid is comprised of a mass spectrometry matrix material and a carrier fluid, and the carrier fluid is comprised of a low volatility solvent that has a boiling point greater than 100° C. at a pressure of 1 atmosphere;
   (b) placing a surface of a sample in droplet-receiving relationship to the fluid-containing reservoir;
   (c) ejecting a droplet of the analysis-enhancing fluid from the reservoir such that the droplet is deposited on the sample surface at a designated site; and
   (d) subjecting the sample to conditions sufficient to allow the analysis-enhancing fluid to interact with the sample surface to render the sample surface suitable for analysis.

42. The method of claim 41, wherein the mass spectrometry matrix material is a photoabsorbing matrix material.

43. The method of claim 42, wherein step (c) is carried out by applying focused acoustic energy to the analysis-enhancing fluid contained in the reservoir in a manner effective to eject a droplet therefrom.

44. The method of claim 43, further comprising, after step (d), (d') bombarding the designated site with photons to release sample molecules from the sample surface for analysis.

45. The method of claim 44, further comprising, after step (d'), (e) performing mass spectrometric analysis on the sample molecules.

46. The method of claim 42, wherein the sample is a cellular sample.

47. The method of claim 41, wherein step (d) comprises subjecting the sample to a temperature greater than 25° C.

48. The method of claim 41, wherein step (d) comprises subjecting the sample to a pressure lower than about 1 atmosphere.

49. A method for preparing a sample surface for mass spectrometry analysis, comprising:
   (a) providing a reservoir containing an analysis-enhancing fluid, wherein the analysis-enhancing fluid is comprised of a mass spectrometry matrix material and a carrier fluid, and the carrier fluid is comprised of a high volatility solvent that has a boiling point lower than 100° C. at a pressure of 1 atmosphere;
   (b) placing a surface of a sample in droplet-receiving relationship to the fluid-containing reservoir;
   (c) ejecting a droplet of the analysis-enhancing fluid from the reservoir such that the droplet is deposited on the sample surface at a designated site; and
   (d) subjecting the sample to a temperature lower than 25° C. and/or a pressure greater than 1 atmosphere to allow the analysis-enhancing fluid to interact with the sample surface and to render the sample surface suitable for analysis.

50. The method of claim 49, wherein the mass spectrometry matrix material is a photoabsorbing matrix material.

51. The method of claim 49, wherein step (c) is carried out by applying focused acoustic energy to the analysis-enhancing fluid contained in the reservoir in a manner effective to eject a droplet therefrom.

52. The method of claim 51, further comprising, after step (d), (d') bombarding the designated site with photons to release sample molecules from the sample surface for analysis.

53. The method of claim 52, further comprising, after step (d'), (e) performing mass spectrometric analysis on the sample molecules.

54. The method of claim 49, wherein the sample is a cellular sample.

55. A method for preparing a sample surface for mass spectrometry analysis, comprising:
   (a) providing a reservoir containing an analysis-enhancing fluid, wherein the analysis-enhancing fluid is comprised of a mass spectrometry matrix material and a carrier fluid;
   (b) placing a surface of a sample in droplet-receiving relationship to the fluid-containing reservoir;
   (c) ejecting a droplet of the analysis-enhancing fluid from the reservoir such that the droplet is deposited on the sample surface at a designated site; and
   (d) subjecting the sample to an atmosphere that is at least about 30% saturated with the carrier fluid to allow the analysis-enhancing fluid to interact with the sample surface and to render the sample surface suitable for analysis.

56. The method of claim 55, wherein the atmosphere is at least about 50% saturated with the carrier fluid.

57. The method of claim 56, wherein the atmosphere is at least about 75% saturated with the carrier fluid.

58. The method of claim 57, wherein the atmosphere is at least about 90% saturated with the carrier fluid.

59. A method for preparing a sample surface for mass spectrometry analysis, comprising:
   (a) providing a reservoir containing an analysis-enhancing fluid, wherein the analysis-enhancing fluid is comprised of a mass spectrometry matrix material and a carrier fluid;
   (b) placing a surface of a sample in droplet-receiving relationship to the fluid-containing reservoir;
   (c) ejecting a droplet of the analysis-enhancing fluid from the reservoir such that the droplet is deposited on the sample surface at a designated site; and
   (d) subjecting the sample to conditions such that the carrier fluid exhibits a volatility quotient of at least about 30 to allow the analysis-enhancing fluid to interact with the sample surface and to render the sample surface suitable for analysis.

60. The method of claim 59, wherein the carrier fluid exhibits a volatility quotient of at least about 50.

61. The method of claim 60, wherein the carrier fluid exhibits a volatility quotient of at least about 75.

62. The method of claim 60, wherein the carrier fluid exhibits a volatility quotient of at least about 100.

63. A system for depositing an analysis-enhancing fluid on a surface of a sample, comprising:
   a reservoir containing an analysis-enhancing fluid, wherein the analysis-enhancing fluid comprises a mass-spectrometry matrix material and a carrier fluid, and the carrier fluid is comprised of a low volatility solvent that has a boiling point greater than 100° C. at a pressure of 1 atmosphere;
   an acoustic ejector comprising an acoustic radiation generator for generating acoustic radiation and a focusing means for focusing the acoustic radiation generated;

a means for positioning the acoustic ejector in acoustic coupling relationship to the reservoir; and a means for positioning the sample such that a designated site on the sample surface is positioned in droplet-receiving relationship to the reservoir.

64. The system of claim 63, wherein the acoustic ejector is adapted to eject a droplet having a volume no greater than about 50 pL.

65. The system of claim 63, further comprising a means for applying energy to the designated site to effect release and ionization of sample molecules from the sample surface for analysis.

66. The system of claim 65, wherein the energy applying means comprises a means for bombarding the at least one selected site with photons.

67. The system of claim 66, wherein the photon bombarding means comprises a laser.

68. The system of claim 65, further comprising an analyzer positioned to receive ionized sample molecules released from the sample surface.

69. The system of claim 68, wherein the analyzer is comprised of a mass spectrometer.

* * * * *